US010687715B2

(12) United States Patent
Jansen et al.

(10) Patent No.: US 10,687,715 B2
(45) Date of Patent: Jun. 23, 2020

(54) NON-INVASIVE INTRAVASCULAR VOLUME INDEX MONITOR

(71) Applicant: Masimo Corporation, Irvine, CA (US)

(72) Inventors: Paul Ronald Jansen, Cardiff by the Sea, CA (US); Michael O'Reilly, Dana Point, CA (US)

(73) Assignee: Masimo Corporation, Irvine, CA (US)

( * ) Notice: Subject to any disclaimer, the term of this patent is extended or adjusted under 35 U.S.C. 154(b) by 338 days.

(21) Appl. No.: 15/388,672

(22) Filed: Dec. 22, 2016

(65) Prior Publication Data

US 2017/0196464 A1    Jul. 13, 2017

Related U.S. Application Data

(62) Division of application No. 13/347,142, filed on Jan. 10, 2012, now Pat. No. 9,579,039.

(60) Provisional application No. 61/431,230, filed on Jan. 10, 2011.

(51) Int. Cl.
| A61B 5/1455 | (2006.01) |
| A61B 5/0205 | (2006.01) |
| A61B 5/103 | (2006.01) |
| A61B 5/00 | (2006.01) |
| A61B 5/053 | (2006.01) |
| A61B 5/145 | (2006.01) |

(52) U.S. Cl.
CPC .......... *A61B 5/0205* (2013.01); *A61B 5/0537* (2013.01); *A61B 5/103* (2013.01); *A61B 5/1455* (2013.01); *A61B 5/14542* (2013.01); *A61B 5/412* (2013.01); *A61B 5/4878* (2013.01); *A61B 5/746* (2013.01); *A61B 5/053* (2013.01); *A61B 5/14551* (2013.01); *A61B 5/7275* (2013.01)

(58) Field of Classification Search
None
See application file for complete search history.

(56) References Cited

U.S. PATENT DOCUMENTS

| 3,802,776 A | 4/1974 | Tchang |
| 4,648,028 A | 3/1987 | DeKlotz et al. |
| 4,834,532 A | 5/1989 | Yount |
| 4,843,013 A | 6/1989 | Chiang |
| (Continued) | | |

FOREIGN PATENT DOCUMENTS

| WO | WO 01/30414 | 5/2001 |
| WO | WO 2014/035588 | 3/2014 |

OTHER PUBLICATIONS

U.S. Appl. No. 61/431,230, filed Jan. 2011, Jansen et al.
(Continued)

*Primary Examiner* — Eric F Winakur
*Assistant Examiner* — Marjan Fardanesh
(74) *Attorney, Agent, or Firm* — Knobbe, Martens, Olson & Bear, LLP

(57) ABSTRACT

A non-invasive electronic patient monitor tracks one or more physiological parameters of a patient, such as intravascular volume index (IVI), extravascular volume index (EVI), total hemoglobin (SpHb), impedance, and/or weight. The patient monitor determines if one or more of the physiological parameters are within a predetermined range. The patient monitor activates an alarm if one or more of the physiological parameters are outside the predetermined range and indicates a patient can be experiencing edema and/or heart failure, or sepsis.

19 Claims, 23 Drawing Sheets

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,101,825 A | 4/1992 | Gravenstein |
| 5,163,438 A | 11/1992 | Gordon et al. |
| 5,193,543 A | 3/1993 | Yelderman |
| 5,278,627 A | 1/1994 | Aoyagi et al. |
| 5,297,548 A | 3/1994 | Pologe |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,575,284 A | 11/1996 | Athan et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,692,503 A | 12/1997 | Kuenstner |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,803,909 A | 9/1998 | Maki |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,912,656 A | 6/1999 | Tham et al. |
| 5,919,134 A | 7/1999 | Diab |
| 5,934,925 A | 8/1999 | Tobler et al. |
| 5,940,182 A | 8/1999 | Lepper, Jr. et al. |
| 5,957,885 A | 9/1999 | Bollish et al. |
| 5,995,855 A | 11/1999 | Kiani et al. |
| 5,997,343 A | 12/1999 | Mills et al. |
| 6,002,952 A | 12/1999 | Diab et al. |
| 6,011,985 A | 1/2000 | Athan |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,174,283 B1 | 1/2001 | Nevo et al. |
| 6,184,521 B1 | 2/2001 | Coffin, IV et al. |
| 6,206,830 B1 | 3/2001 | Diab et al. |
| 6,223,064 B1 | 4/2001 | Lynn et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,282,438 B1 | 8/2001 | Maki et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,473,632 B1 | 10/2002 | Myers |
| 6,496,711 B1 | 12/2002 | Athan et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,611,320 B1 | 8/2003 | Lindberg |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,528 B2 | 12/2003 | Steuer et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |

(56) References Cited

U.S. PATENT DOCUMENTS

| | | |
|---|---|---|
| 6,745,060 B2 | 6/2004 | Diab et al. |
| 6,760,607 B2 | 7/2004 | Al-Ali |
| 6,763,256 B2 | 7/2004 | Kimball et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,842,639 B1 | 1/2005 | Winston et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,879,850 B2 | 4/2005 | Kimball |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,763 B2 | 1/2006 | Boas |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,142,902 B2 | 11/2006 | Eda et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,319,894 B2 | 1/2008 | Higgins |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,426,407 B2 | 9/2008 | Higgins |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,744,541 B2 | 6/2010 | Baruch et al. |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,826,890 B1 | 11/2010 | Winchester, Jr. et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |

(56) References Cited

U.S. PATENT DOCUMENTS

| | | |
|---|---|---|
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |

(56) References Cited

U.S. PATENT DOCUMENTS

| | | |
|---|---|---|
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,686 B2 | 5/2016 | Warren et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,370,325 B2 | 6/2016 | Al-Ali et al. |
| 2001/0035503 A1* | 11/2001 | Quistorff ............ A61B 5/0059 250/495.1 |
| 2003/0106553 A1 | 6/2003 | Vanderveen |
| 2004/0034293 A1 | 2/2004 | Kimball et al. |
| 2004/0034294 A1 | 2/2004 | Kimball et al. |
| 2004/0102712 A1 | 5/2004 | Belalcazar et al. |
| 2004/0122300 A1 | 6/2004 | Boas |
| 2004/0152956 A1 | 8/2004 | Korman |
| 2005/0019936 A1 | 1/2005 | Samsoondar |
| 2005/0277819 A1 | 12/2005 | Kiani et al. |
| 2006/0149144 A1 | 7/2006 | Lynn et al. |
| 2006/0189871 A1 | 8/2006 | Al-Ali et al. |
| 2006/0217628 A1 | 9/2006 | Huiki |
| 2007/0088222 A1 | 4/2007 | Berkow et al. |
| 2007/0093701 A1 | 4/2007 | Myers |
| 2007/0282478 A1 | 12/2007 | Al-Ali et al. |
| 2008/0030468 A1 | 2/2008 | Ali et al. |
| 2008/0064965 A1 | 3/2008 | Jay et al. |
| 2008/0097173 A1 | 4/2008 | Soyemi et al. |
| 2009/0247924 A1 | 10/2009 | Lamego et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0281839 A1 | 11/2009 | Lynn et al. |
| 2009/0299157 A1 | 12/2009 | Telfort et al. |
| 2009/0326342 A1 | 12/2009 | Huiki |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0198029 A1 | 8/2010 | Wang |
| 2010/0261979 A1 | 10/2010 | Kiani |
| 2010/0298675 A1 | 11/2010 | Al-Ali |
| 2011/0001605 A1 | 1/2011 | Kiani et al. |
| 2011/0028809 A1 | 2/2011 | Goodman |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0190613 A1 | 8/2011 | Zhang |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0288383 A1 | 11/2011 | Diab |
| 2011/0301444 A1 | 12/2011 | Al-Ali |
| 2012/0029301 A1 | 2/2012 | Battista |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0116175 A1 | 5/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0209095 A1 | 8/2012 | Huiki |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0289797 A1 | 11/2012 | Al-Ali |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0006076 A1 | 1/2013 | McHale |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |

(56) References Cited

U.S. PATENT DOCUMENTS

| | | |
|---|---|---|
| 2013/0060108 A1 | 3/2013 | Schurman et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243625 A1 | 8/2014 | Warren |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0045685 A1 | 2/2015 | Al-Ali et al. |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099324 A1 | 4/2015 | Wojtczuk et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |

(56) References Cited

U.S. PATENT DOCUMENTS

2016/0113527 A1     4/2016   Al-Ali et al.
2016/0143548 A1     5/2016   Al-Ali

OTHER PUBLICATIONS

U.S. Appl. No. 15/184,950, filed Jun. 2016, Al Ali et al.

M. Cannesson, O. Desebbe, P. Rosamel, B. Delannoy, J. Robin, O. Bastein, and J.-J. Lehot Pleth variability index to monitor the respiratory variations in the pulse oximeter plethysmographic waveform amplitude and predict fluid responsiveness in the operating theatre Br. J. Anaesth. (2008) 101(2): 200-206 first published online Jun. 2, 2008 doi:10.

Feissel, Marc Teboul, Jean-Louis Merlani, Paolo Badie, Julio Faller, Jean-Pierre Bendjelid, Karim "Plethysmographic dynamic indices predict fluid responsiveness in septic ventilated patients" Intensive Care Medicine Jun. 1, 2007 Springer Berlin / Heidelberg 993-999 33:6.

Ursula Wolf et al.; Journal of Biomedical Optics; "Correlation of functional and resting state connectivity of cerebral oxydeoxy-, and total hemoglobin concentration changes measured by near-infrared spectrophotometry."; Aug. 3, 2011.

John E. Scharf, MD et al.; Leeexplore; USF Department of Anesthesiology; USF Department of Electrical Engineering; Optimization of Portable Pulse Osimetry Through Fouriuer Analysis, 1993.

Jared S. Ruckman; University of Connecticut; A Comparative Study of Total Hemoglobin Measurement Technology; Noninvasive Pulse Cooximetry and Conventional Methods (Masters Thesis); May 7, 2011.

\* cited by examiner

NON-INVASIVE INTRAVASCULAR VOLUME INDEX MONITOR

CROSS-REFERENCE TO RELATED APPLICATIONS

The present application is a divisional of U.S. patent application Ser. No. 13/347,142, filed Jan. 10, 2012, entitled "Non-Invasive Intravascular Volume Index Monitor," which claims priority benefit of U.S. Provisional Patent Application No. 61/431,230, filed Jan. 10, 2011, entitled "Non-Invasive Total Hemoglobin Monitor," each of which is hereby incorporated by reference herein in its entirety.

The present application is related to U.S. patent application Ser. No. 12/560,331, filed Sep. 15, 2009, entitled "Hemoglobin Monitor," and U.S. patent application Ser. No. 12/783,436, now U.S. Pat. No. 8,571,619, filed May 19, 2010, entitled "Hemoglobin Display and Patient Treatment," each of which is hereby incorporated by reference herein in its entirety.

BACKGROUND

Generally described, heart failure is the inability of the heart to supply sufficient blood flow to meet the body's needs. Heart failure can significantly reduce the quality of life of a patient and lead to death. Generally, heart failure is the result of the weakening or hardening of one or both ventricles of the heart. Whether weakened or hardened, one or both ventricles do not pump sufficient amounts of blood and fluids through the body. As a result, excessive fluid can build up in different locations within the body depending on which ventricle is affected. This build up of liquids can lead to serious side effects, such as dyspnea (shortness of breath), impaired liver function, ascites (fluid accumulation in the abdominal cavity), pulmonary edema (excessive fluid in the lungs), dependent peripheral edema (excessive fluid in the organs and extremities), pleural effusion (fluid collection between the lung and chest wall), coagulopathy, and can be life threatening.

Generally described, sepsis is a serious medical condition that is characterized by a whole-body inflammatory state (systemic inflammatory response syndrome or SIRS) in response to an infection. The immune system's reaction to the infection may injure the body tissues far from the original infection. As sepsis progresses, it begins to affect organ function and eventually can lead to septic shock a sometimes fatal drop in blood pressure. For certain individuals with other medical conditions, the fatality rate for sepsis can be as high as 60%. Thus, diagnosing and treating sepsis early and accurately is extremely important to improve the survivability of the patient.

In addition, treating sepsis can be extremely expensive because a patient is often treated in an intensive care unit (ICU) for several days or weeks. Sepsis can often be diagnosed using blood culture, analyzing blood gases, kidney function tests that are abnormal, platelet counts that are lower than normal, and/or white blood cell counts that are lower or higher than normal. Other tests may include urine tests, wound secretions, cerebrospinal fluid tests, X-rays, computerized tomography (CT) scans, ultrasounds, and/or magnetic resonance imaging (MRI) scans. Patients diagnosed with or suspected of having sepsis are often admitted to the ICU for treatment. Treatment typically involves intravenous antibiotic therapy, as well as oxygen, intravenous fluids and medications that increase blood pressure, and can last several days or even weeks. Additional treatment may include draining any abscesses, breathing machine, and/or dialysis.

SUMMARY

Generally speaking, diagnosing and/or monitoring the progression of heart failure can be a difficult process that requires multiple visits to a doctor's office or hospital as well as multiple blood samples, tests, and the like. The blood sample and tests can be analyzed to determine if there is excessive fluid buildup within the body. To help remove the excess fluids a patient will often be given a diuretic. One problem that arises with the administration of a diuretic is that it is difficult to know when sufficient amounts of a liquid have been removed and thus when to stop providing the diuretic. Failure to remove the liquids can result in continued edema. On the other hand, removing too much fluid can result in dehydration. Currently, the person administering the diuretic often must guess or estimate the appropriate amount of drug to administer and when to stop.

Similarly, monitoring the treatment of sepsis after diagnosis can also be difficult. As mentioned above, after diagnosis of sepsis, treatment is typically initiated with fluid administration. Ineffective fluid management can lead to organ dysfunction, which can result in longer hospitals stays and even death. Fluid management is often guided by central venous pressure (CVP), however, CVP is not known to be accurate at indicating a need for or a response to fluid administration. In other words, clinicians can keep track of how much fluid goes in, but struggle knowing whether the fluid is staying in the intravascular space and when to stop administering fluid. An accurate assessment of intravascular and extravascular volume would therefore significantly aid fluid management.

An intravascular volume index (IVI) can indicate a relative amount of fluid levels in the intravascular space of a patient, and help a user track fluid levels of the patient. Thus, one or more intravascular volume indices can be used in both the detection and treatment of edema and sepsis. Additional and/or alternative physiological parameters can be used to monitor fluid levels in the intravascular space and detect edema and sepsis. For example, total hemoglobin (SpHb), extravascular volume index (EVI), impedance, and/or weight can be used to detect edema and/or sepsis in a patient.

DETAILED DESCRIPTION

Figure 1A:
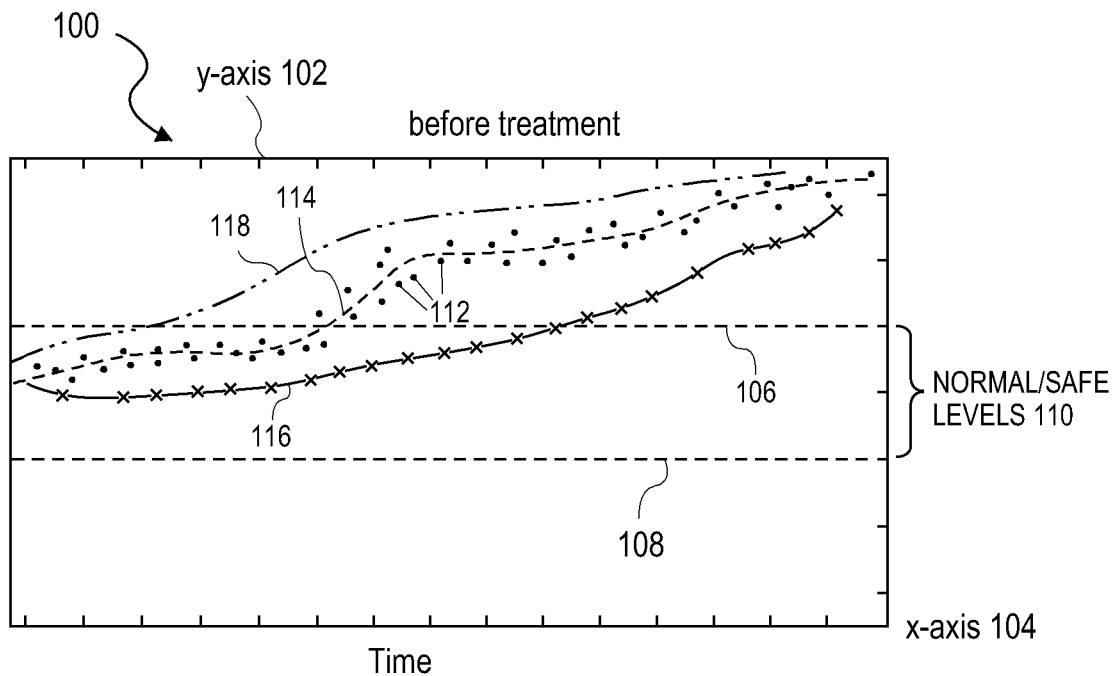
FIG. 1A illustrates an example of IVI levels over time of a patient experiencing edema.

Blood is made up of red blood cells, white blood cells, platelets, and plasma. Plasma typically makes up approximately 55% of blood volume, sometimes referred to as effective plasma volume or intravascular volume. The remaining blood volume is mostly made up of red blood cells, which is also referred to as the hematocrit. The typical hematocrit for men and women is approximately 48% and 38%, respectively. Normally, the hematocrit is determined by centrifuging heparinized blood. However, the hematocrit can also be approximated by multiplying the total hemoglobin concentration (SpHb) by three. IVI can be approximated by subtracting the hematocrit from 100. Put another way, hematocrit≈SpHb*3, and IVI≈100−hematocrit or 100−(SpHb*3).

Additionally, IVI can be monitored by tracking the amount of light absorbed by a patient's finger, toe, foot, ear, or other extremity where blood flows near the surface of the skin and sufficient light is able to pass through and be detected by the detector. Intravascular fluid with greater concentrations of hemoglobin absorb greater amounts of light, while intravascular fluid with less hemoglobin absorb lesser amounts of light. This relationship between light absorption and hemoglobin concentrations can be used to monitor the IVI of a patient generally. For example, as the amount of light absorbed trends up or down, the patient monitor can determine that hemoglobin concentration is trending up or down, respectively, and IVI is trending down or up, respectively. Similarly, an increase in the amount of light detected by a detector indicates a decrease in hemoglobin concentration, and a decrease in the amount of light detected by the detector indicates an increase in hemoglobin concentration. In some embodiments IVI is determined without calculating SpHb.

Typically, total hemoglobin concentration (SpHb) ranges from 13-19 g/dL for adult males and 12-16 g/dL for adult females. However, with heart failure, as liquids accumulate, SpHb levels can decrease below normal levels. The administration of a diuretic can decrease fluid levels, thereby returning SpHb to normal levels. As mentioned above, if too little diuretic is administered the patient continues to experience edema, however, too much diuretic can result in a dangerously high SpHb and dehydration. Thus, it is important to administer the correct amount of diuretic to treat a patient for edema.

The device described herein can track one or physiological parameters of a patient including, but not limited to, EVI, PVI, SpHb, impedance, weight, etc. Using the trends of the physiological parameters, the system can detect edema and/or sepsis, and can be used during treatment of the same. In some embodiments, one system can be used for the detection of both edema and sepsis. In certain embodiments, one system can be used to detect, and during the treatment of, edema, while another system can be used to detect, and during the treatment of, sepsis.

As edema and heart failure often take several days or weeks to develop, in some embodiments, the system can be configured for home use. The monitoring system can include the sensors used to track IVI, EVI, PVI, and/or SpHb, impedance sensors to track the patient's impedance and/or a scale to track the patient's weight. Accordingly, the system can measure all the physiological parameters of the patient used to detect edema and/or heart failure, and record the measurements. In some embodiments, the system monitors fewer or more physiological parameters. In certain embodiments, a user can manually enter one or more physiological parameters into the system. The system can analyze the measurements of individual physiological parameters or combinations of multiple physiological parameters and alert a user or healthcare provider in the event an abnormal condition is detected in one or more of the physiological parameters. The system can be calibrated for a user and use threshold values or a heuristic approach to determine if an abnormal condition has occurred. In some embodiments, the system provides the measurements to the user or healthcare provider to assess changes to the physiological parameters. A system configured for hospital use can include the same functionality, or can be configured to monitor fewer or less physiological parameters.

Similarly, a system configured to detect, and monitor the treatment of, sepsis can be configured for home use or hospital use. The system can include sensors used to track IVI, PVI, and/or SpHb. Additional sensors can also be used to track EVI, the patient's impedance, and/or weight.

In some embodiments, the patient monitor can identify edema upon detecting an increase in IVI and/or a decrease in SpHb levels. The patient monitor can also track the weight of the patient and the impedance of the patient. An increase in weight and/or increase in impedance can also indicate edema and/or heart failure. During treatment, the patient monitor can continue tracking one or more physiological parameters to identify a safe range or threshold to terminate treatment. Thus, the system can be used in diagnosing, monitoring the progression of, and during treatment of edema.

In certain embodiments, the system identifies a patient at risk of, or suffering from, sepsis by detecting a decrease in the IVI and/or an increase in SpHB levels. The system can also track the impedance of the patient using impedance monitors to determine the impedance (either whole body or segmental) of the patient. The impedance can be used to determine EVI and/or changes in EVI. Other methods can also be used to monitor EVI. By monitoring one or more physiological parameters, such as IVI, EVI, PVI, and/or SpHb during sepsis treatment, the system can improve treatment, reduce hospital stays, and decrease fatality rates.

Figure 1B:
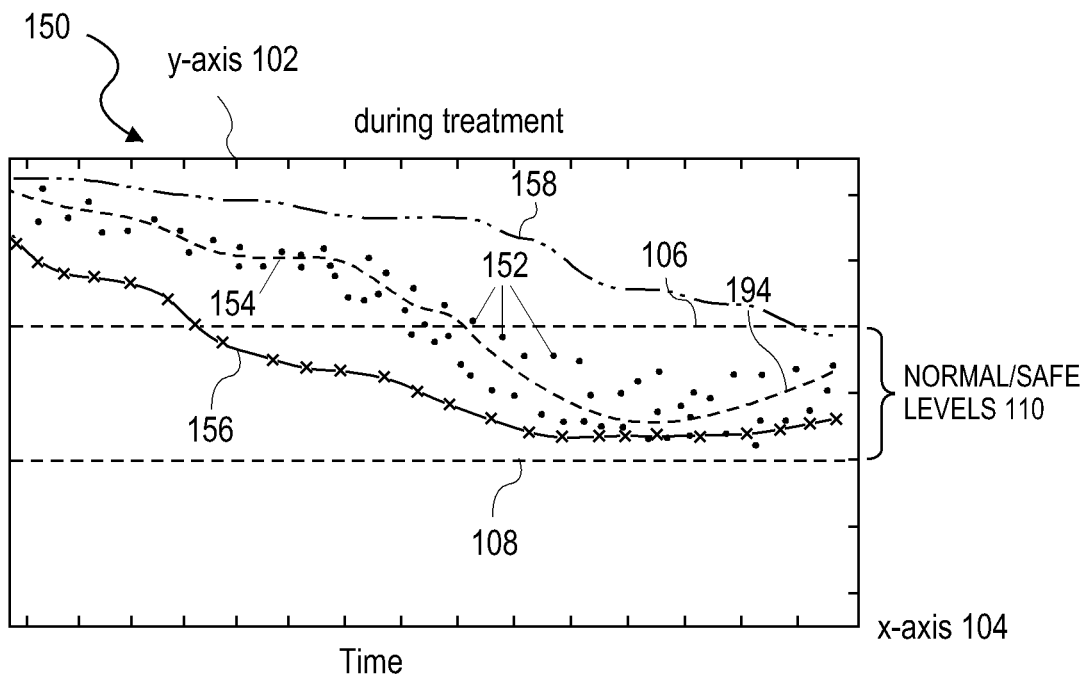
FIG. 1B illustrates an example of IVI levels of a patient upon administration of a diuretic.

FIGS. 1A and 1B illustrate examples of SpHb levels of patients experiencing edema, which can be caused by heart failure.

FIG. 1A illustrates a graph 100 showing an example of the trends multiple physiological parameters of a patient experiencing edema. The physiological parameters and corresponding trend lines can include, but are not limited to IVI 114, impedance 116, and weight 118.

The y-axis 102 represents the different units of the various physiological parameters, and the x-axis 104 represents time. In some embodiments, the y-axis 102 is a normalization of the various physiological parameters. The time indicated by the x-axis 104 can be any number of different increments. In some embodiments, the increments are days or weeks. In certain embodiments, the increments can be hours or even minutes. The various dots 112 in FIG. 1A indicate discrete measurements of IVI at a specific time. In some embodiments, the measurements 112 can be taken every few hours or days. In certain embodiments, measurements 112 can be taken every few seconds or minutes, and can appear as one continuous line. Additional dots can be used to represent discrete measurements of other physiological parameters.

An IVI trend line 114 shows the trends of IVI. The IVI trend line 114 can indicate a total, specific, or normalized value of IVI and/or indicate a rate of change of IVI levels. The graph 100 further includes a high threshold 106 and a low threshold 108. The area between the high threshold 106 and low threshold 108 represents a normal or safe zone 110. IVI measurements that are within the normal or safe zone 110 indicate a person has a normal or safe IVI. In certain embodiments, the threshold levels can be based on previous tracked levels of the individual being measured. For example, a statistical analysis of the patient's IVI levels can be used to determine the appropriate threshold levels. The measurements can also be normalized and/or can indicate relative changes to a patient's IVI. In some embodiments, the different threshold levels can be set based on typical IVIS of similarly situated patients e.g. based on sex, age, etc.

IVI can vary over time, and can gradually change over a number of days, weeks, or months. In some instances, IVI can change precipitously within a number of minutes, or less. As discussed above, one cause of the variation can be due to edema caused by heart failure or some other condition. As shown in FIG. 1A, the effects of edema, or other conditions can cause IVI to rise above normal or safe levels and lead to the above-described side effects.

The impedance trend line 116 and weight trend line 118 show trends in a patients impedance and weight, respectively, which can also be used to identify edema and/or heart failure. The impedance trend line 116 and weight trend line 118 can indicate a total, specific, or normalized value and/or indicate a rate of change of impedance and/or weight levels. Although illustrated as continuous lines, the impedance trend line 116 and weight trend line 118 can include discrete measurements, similar to the discrete IVI measurements 112. In some embodiments, the impedance is whole body. In certain embodiments, the impedance is segmental. Similar safe zones 110 can be added for the patient's impedance and weight levels. In some embodiments, the various physiological parameters are normalized and the safe zone 110 is applicable to the various physiological parameters. An increased IVI in conjunction with increased impedance and/or weight levels can be used to increase the confidence that a user is experiencing edema.

FIG. 1B illustrates a graph 150 showing an example of measured IVI levels 152 of a patient upon administration of a diuretic. Similar to FIG. 1A, the y-axis 102 of FIG. 1B represents units for IVI, impedance and weight levels and the x-axis represents time 104. In addition, graph 150 includes a high threshold 106, a low threshold 108, a normal or safe zone 110, an IVI trend line 154, impedance trend line 156, and weight trend line 158. As mentioned above, the IVI trend line 154 can indicate a total, specific, or normalized value of IVI and/or indicate a rate of change of IVI levels. The impedance trend line 156 and weight trend line 158 can be similarly configured. As discussed previously, a patient experiencing edema can be administered a diuretic to decrease the amount of excess fluids in the body. Upon administering a diuretic, IVI, impedance, and weight can return to normal levels 110. If too little diuretic is administered, then the patient can continue to experience the effects of edema, while too much diuretic can cause dehydration, among other conditions.

Figure 1C:
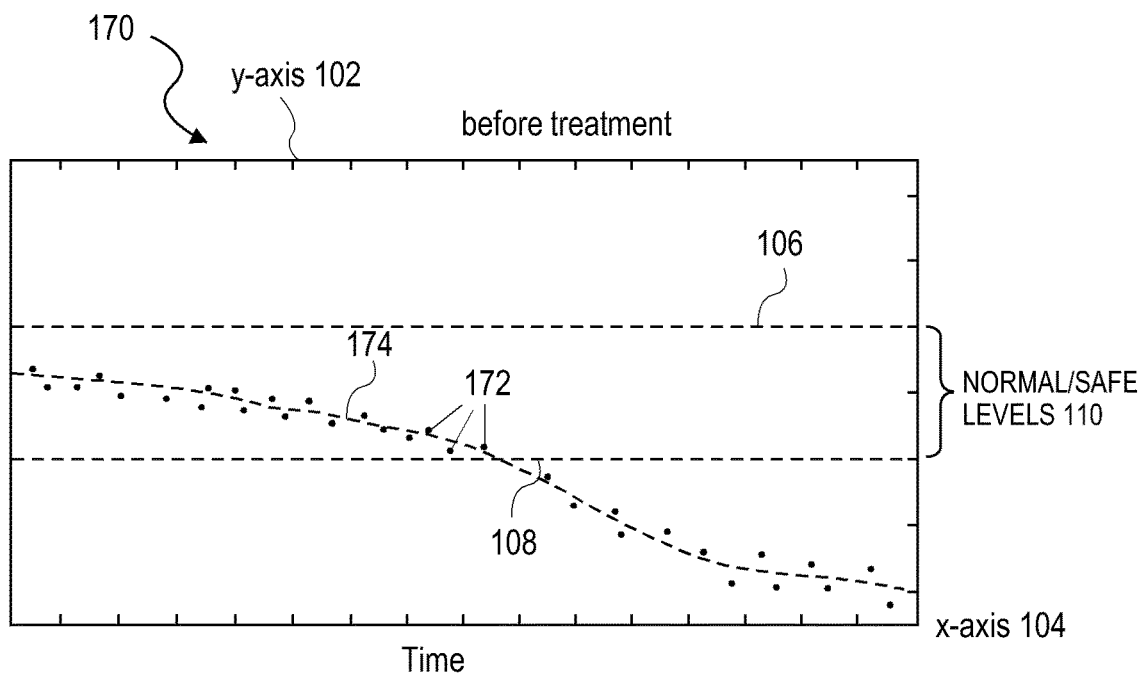
FIG. 1C illustrates an example of IVI levels over time of a patient experiencing sepsis.

FIG. 1C illustrates a graph 170 showing an example of measured IVI levels over time of a patient experiencing sepsis. The y-axis 102 represents the measured IVIS. The x-axis 104 represents time. The time indicated by the x-axis 104 can be in any number of different increments including minutes, hours, days, weeks, etc. The various dots 172 in FIG. 1C indicate discrete measurements of IVIS at a specific time. These measurements can be taken every few seconds, minutes, hours, days, etc. A trend line 174 can show how the IVI levels are trending. The trend line 174 can indicate a total, specific, or normalized value of IVI and/or indicate a rate of change of IVI levels. Alternatively, the measurements 172 can be taken several times each second and can appear as one continuous line, similar to trend line 174. The graph 170 further includes a high threshold level of SpHb 106 and a low threshold level of SpHb 108. The area between the high threshold 106 and low threshold 108 represents a normal or safe zone 110. Measurements that are within the normal or safe zone 110 indicate a person has a normal or safe IVI. The different threshold levels can be set in a variety of ways as described above with reference to FIG. 1A.

As discussed previously, the IVI can vary over time. One cause of the variation can be due to sepsis. As shown in FIG. 1C, the effects of sepsis can cause the IVI to move below normal or safe levels 110 and lead to the above-described side effects. Although not illustrated in FIG. 1C, another side effect of sepsis is inflammation and an increase in extravascular volume. Although not illustrated in FIG. 1C, changes in extravascular volume can also be tracked and used to more accurately identify sepsis. One method to track extravascular volume is by measuring the impedance of a patient.

Figure 1D:
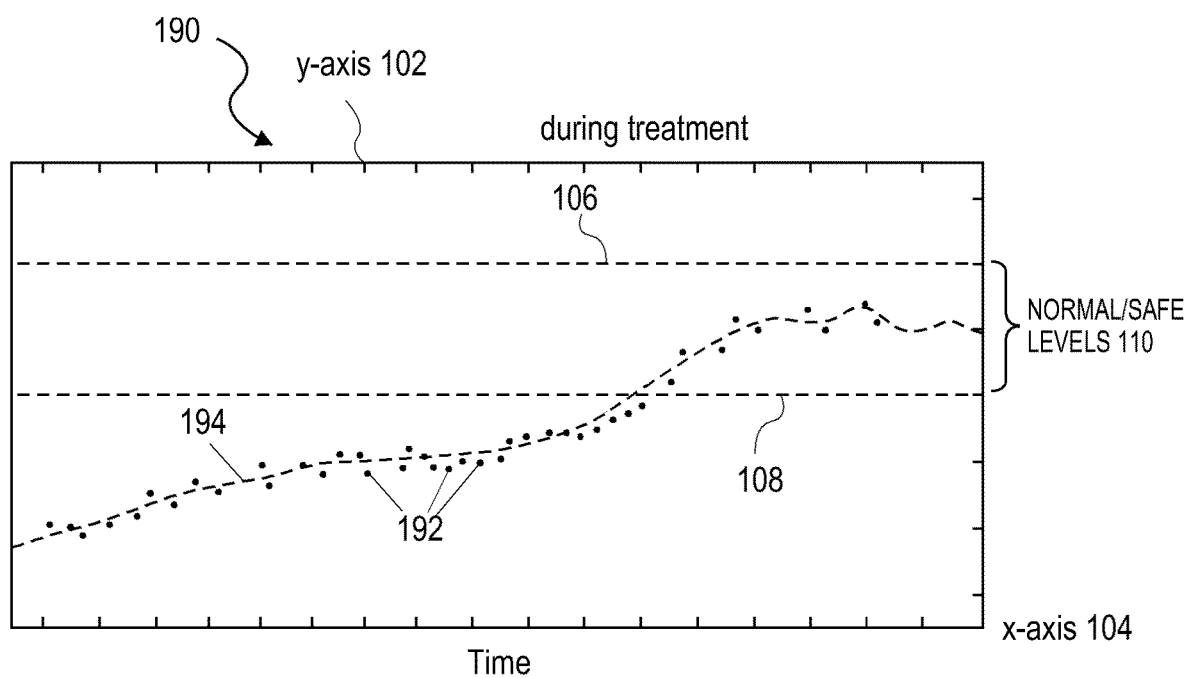
FIG. 1D illustrates an example of IVI levels of a patient during treatment of sepsis.

FIG. 1D illustrates a graph 190 showing an example of measured SpHb levels 192 of a patient during treatment sepsis, such as of intravenous fluids. Similar to FIG. 1C, the y-axis 102 of FIG. 1D represents IVI levels and the x-axis represents time 104. Similarly, graph 190 includes a high threshold 106, a low threshold 108, a normal or safe zone 110, and a trend line 194. The trend line 194 can be similar to the trend line 172, discussed above. As discussed previously, a patient experiencing sepsis can be administered IV fluids to increase the intravascular volume. Upon administering IV fluids, IVI levels can return to normal levels 110. If too little IV fluids are administered, then the patient can continue to experience the effects of sepsis. Thus, it is important to determine when to terminate administering the IV fluids.

Figure 2A:
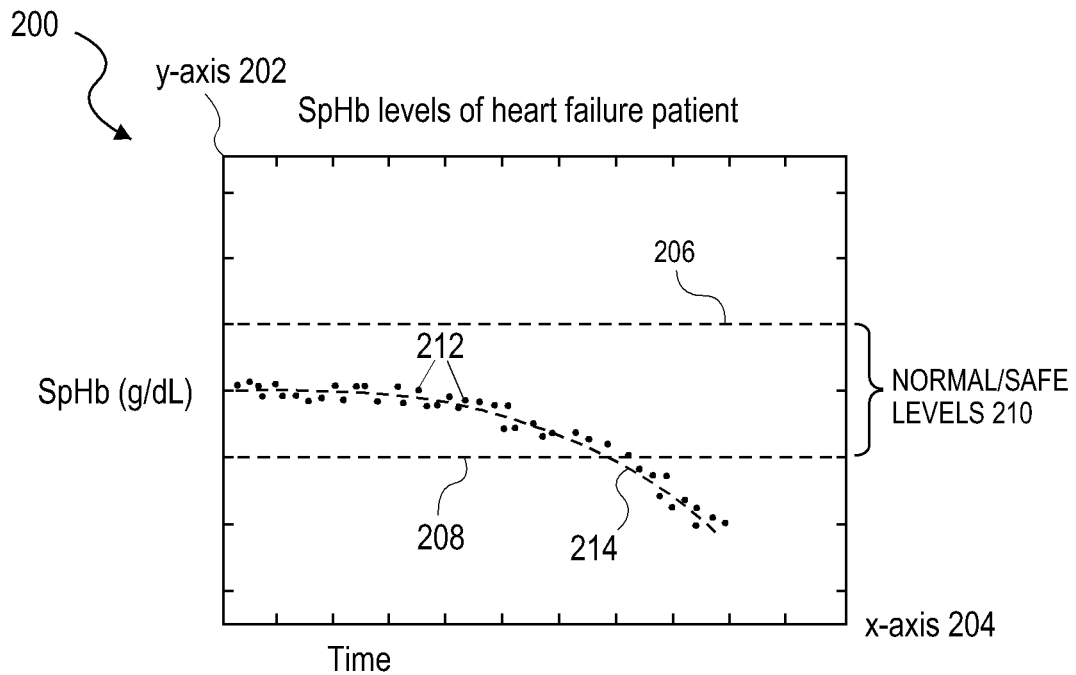
FIG. 2A illustrates an example of SpHb levels over time of a patient experiencing edema.

FIG. 2A illustrates a graph 200 showing an example of measured SpHb levels over time of a patient experiencing edema. The y-axis 202 represents the measured concentration levels of SpHb in g/dL. The x-axis 204 represents time. The time indicated by the x-axis 204 can be in any number of different increments including minutes, hours, days, weeks, etc. The various dots 112 in FIG. 2A indicate discrete measurements of SpHb levels at a specific time. These measurements can be taken every few seconds, minutes, hours, days, etc, A trend line 214 can show how the SpHb levels are trending. The trend line 214 can indicate a total, specific, or normalized SpHb levels and/or a rate of change of SpHb levels. In some embodiments, the trend line 214 indicates relative changes in SpHb levels. Alternatively, the measurements 112 can be taken several times each second and can appear as one continuous line, similar to trend line 214. As mentioned above, the SpHb levels typically range between 13-19 g/dL for adult males and 12-16 g/dL for adult females, but can vary from person to person. The graph 200 further includes a high threshold level of SpHb 206 and a low threshold level of SpHb 208. The area between the high threshold 206 and low threshold 208 represents a normal or safe zone 210. Measurements that are within the normal or safe zone 210 indicate a person has a normal or safe level of SpHb. The different threshold levels can be set in a variety of ways as described above with reference to FIG. 1A.

As discussed in U.S. patent application Ser. No. 12/783, 436, previously incorporated by reference in its entirety, it has been noted that SpHb levels vary over time, and can gradually change over a number of days, weeks, or months. In some cases, the SpHb levels can change precipitously within a number of minutes, or less. As discussed above, one cause of the variation can be due to edema caused by heart failure or some other condition. As shown in FIG. 2A, the effects of edema, or other conditions can cause the SpHb levels to drop below normal or safe levels and lead to the above-described side effects. Although not illustrated in FIG. 2A, another effect of edema is weight gain and an increase in impedance. Although not illustrated in FIG. 2A, these parameters can also be tracked and used to more accurately identify edema and/or heart failure similar to FIG. 1A described above.

Figure 2B:
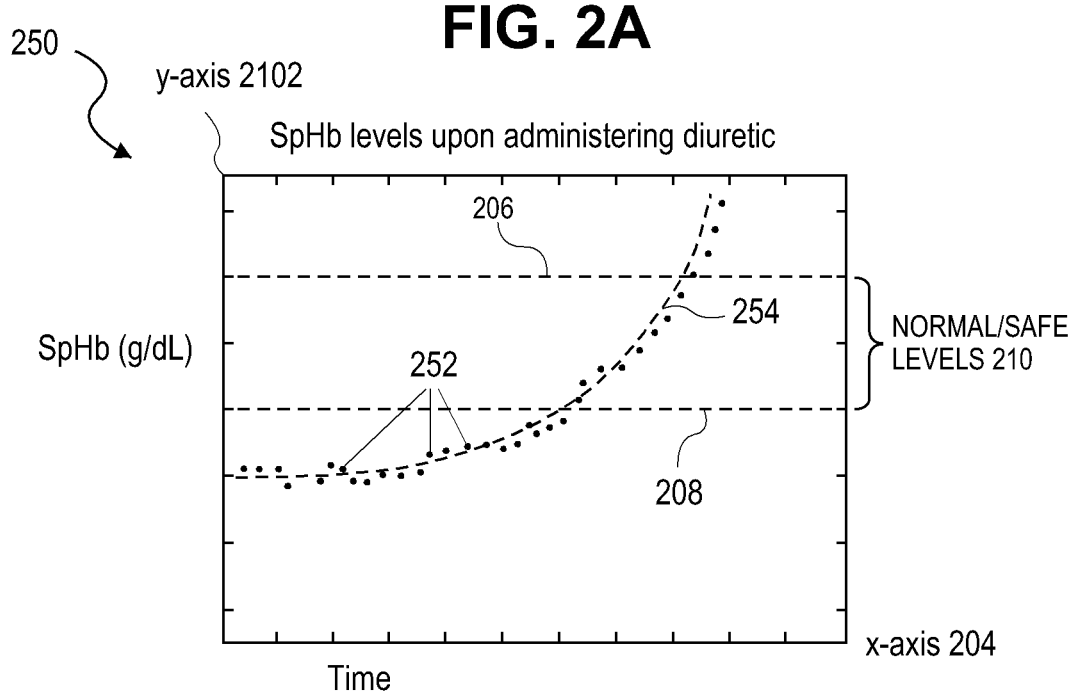
FIG. 2B illustrates an example of SpHb levels of a patient upon administration of a diuretic.

FIG. 2B illustrates a graph 250 showing an example of measured SpHb levels 252 of a patient upon administration of a diuretic, Although not illustrated in FIG. 2B, the graph 250 can include additional physiological parameters that can be monitored as described above with reference to FIG. 1A. Also similar to FIG. 2A, the y-axis 202 of FIG. 2B represents SpHb levels and the x-axis represents time 204. Similarly, graph 250 includes a high threshold of SpHb levels 206, a low threshold of SpHb levels 208, a normal or safe zone 210, and a trend line 254. As mentioned above, the IVI trend line 254 can indicate a total, specific, or normalized value of IVI and/or indicate a rate of change of IVI levels. As discussed previously, a patient experiencing edema can be administered a diuretic to decrease the amount of excess fluids in the body. It has been noted that upon administering a diuretic, IVI levels can return to normal levels 210. If too little diuretic is administered, the patient can continue to experience the effects of edema. Alternatively, too much diuretic can cause dehydration, among other conditions. Thus, it is important to determine when to terminate administering the diuretic.

Figure 2C:
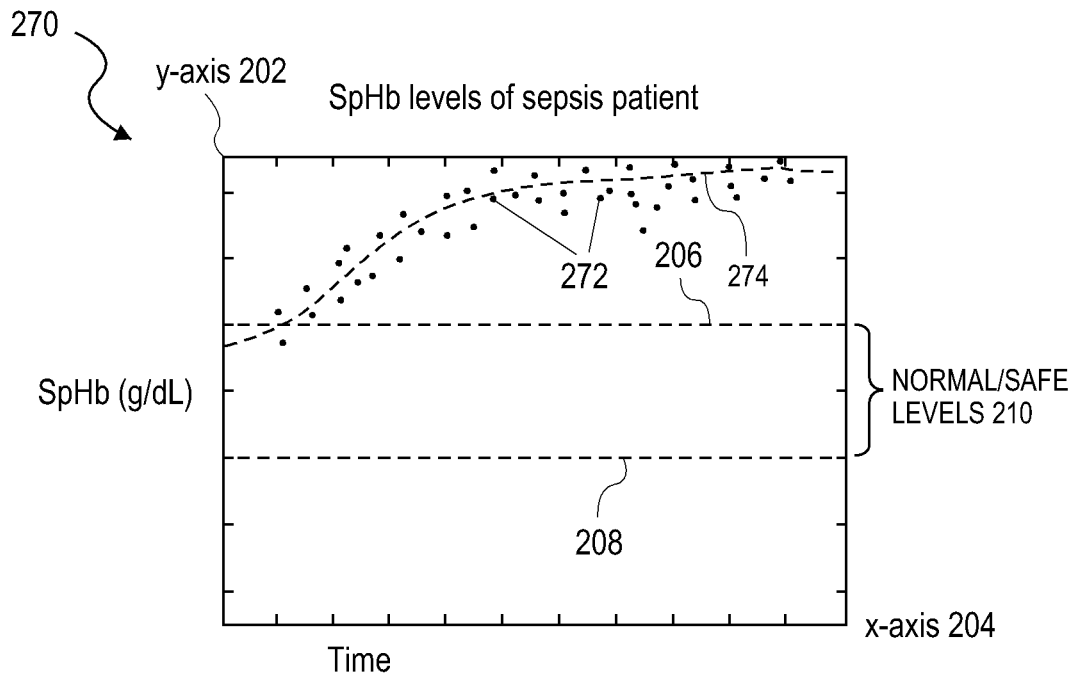
FIG. 2C illustrates an example of SpHb levels over time of a patient experiencing sepsis.

FIG. 2C illustrates a graph 270 showing an example of measured SpHb levels over time of a patient experiencing sepsis. Although not illustrated in FIG. 2C, the graph 270 can include additional physiological parameters as described above with reference to FIG. 1A. The y-axis 202 represents the measured concentration levels of SpHb in g/dL. The x-axis 204 represents time. The time indicated by the x-axis 204 can be in any number of different increments including minutes, hours, days, weeks, etc. The various dots 272 in FIG. 2C indicate discrete measurements of SpHb levels at a specific time. These measurements can be taken every few seconds, minutes, hours, days, etc. A trend line 274 can show how the Spit) levels are trending. The trend line 274 can indicate a total, specific or normalized value of the SpHb levels and/or a rate of change of SpHb levels. In some embodiments, the trend line 274 indicates relative changes to SpHb levels. In certain embodiments, the measurements 272 can be taken several times each second and can appear as one continuous line, similar to trend line 274. As mentioned above, the SpHb levels typically range between 13-19 g/dL for adult males and 12-16 g/dL for adult females, but can vary from person to person. The graph 270 further includes a high threshold level of SpHb 206 and a low threshold level of SpHb 208. The area between the high threshold 206 and low threshold 208 represents a normal or safe zone 210. Measurements that are within the normal or safe zone 210 indicate a person has a normal or safe level of SpHb. The different threshold levels can be set based on typical SpHb levels of similarly situated patients e.g. based on sex, age, etc. Alternatively, the threshold levels can be based on previous tracked levels of the individual being measured.

As discussed previously, SpHb levels vary over time, and one cause of the variation can be due to sepsis. As shown in FIG. 2C, the effects of sepsis can cause the SpHb levels to move above normal or safe levels and lead to the above-described side effects. Although not illustrated in FIG. 2C, another side effect of sepsis is inflammation and an increase in extravascular volume. Changes in extravascular volume can also be tracked and used to more accurately identify sepsis. One method to track extravascular volume is by measuring the impedance of a patient.

Figure 2D:
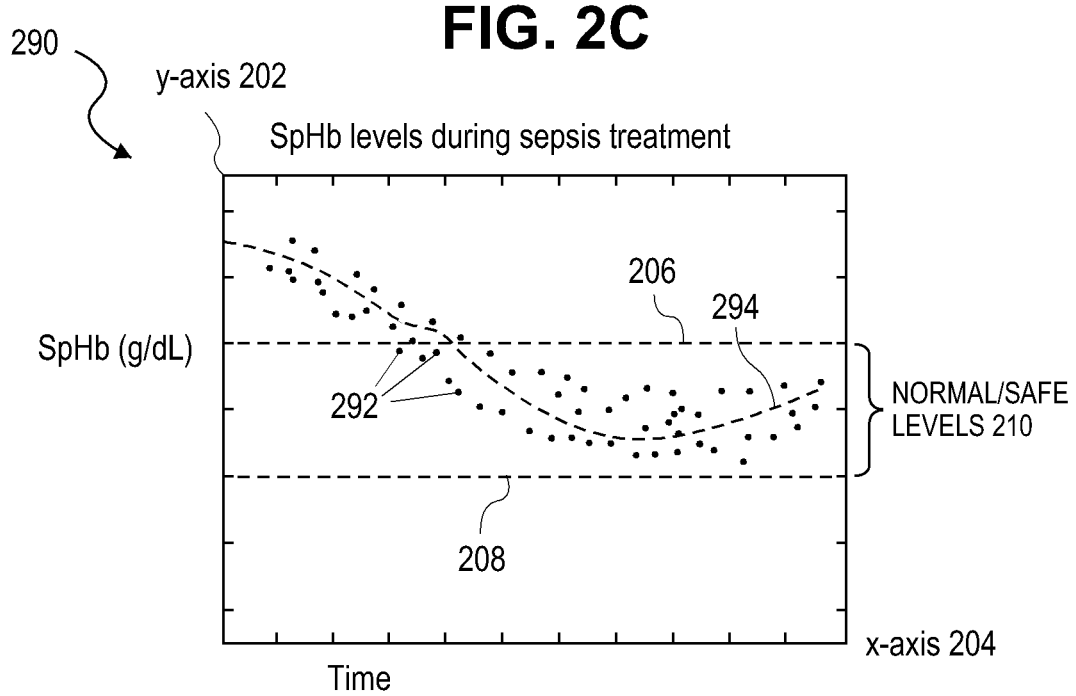
FIG. 2D illustrates an example of SpHb levels of a patient during treatment of sepsis.

FIG. 2D illustrates a graph 290 showing an example of measured SpHb levels 292 of a patient upon administration of intravenous fluids. Similar to FIG. 2C, the y-axis 202 of FIG. 2D represents SpHb levels and the x-axis represents time 204. Similarly, graph 290 includes a high threshold of SpHb levels 206, a low threshold of SpHb levels 208, a normal or safe zone 210, and a trend line 294. As mentioned above, the trend line can indicate a total, specific, or normalized value of SpHb levels and/or indicate a rate of change of SpHb levels. As discussed previously, a patient experiencing sepsis can be administered IV fluids to increase the intravascular volume. Upon administering IV fluids, SpHb levels can return to normal levels 210. If too little IV fluids are administered, then the patient can continue to experience the effects of sepsis. Thus, it is important to determine when to terminate administering the IV fluids.

Figure 3A:
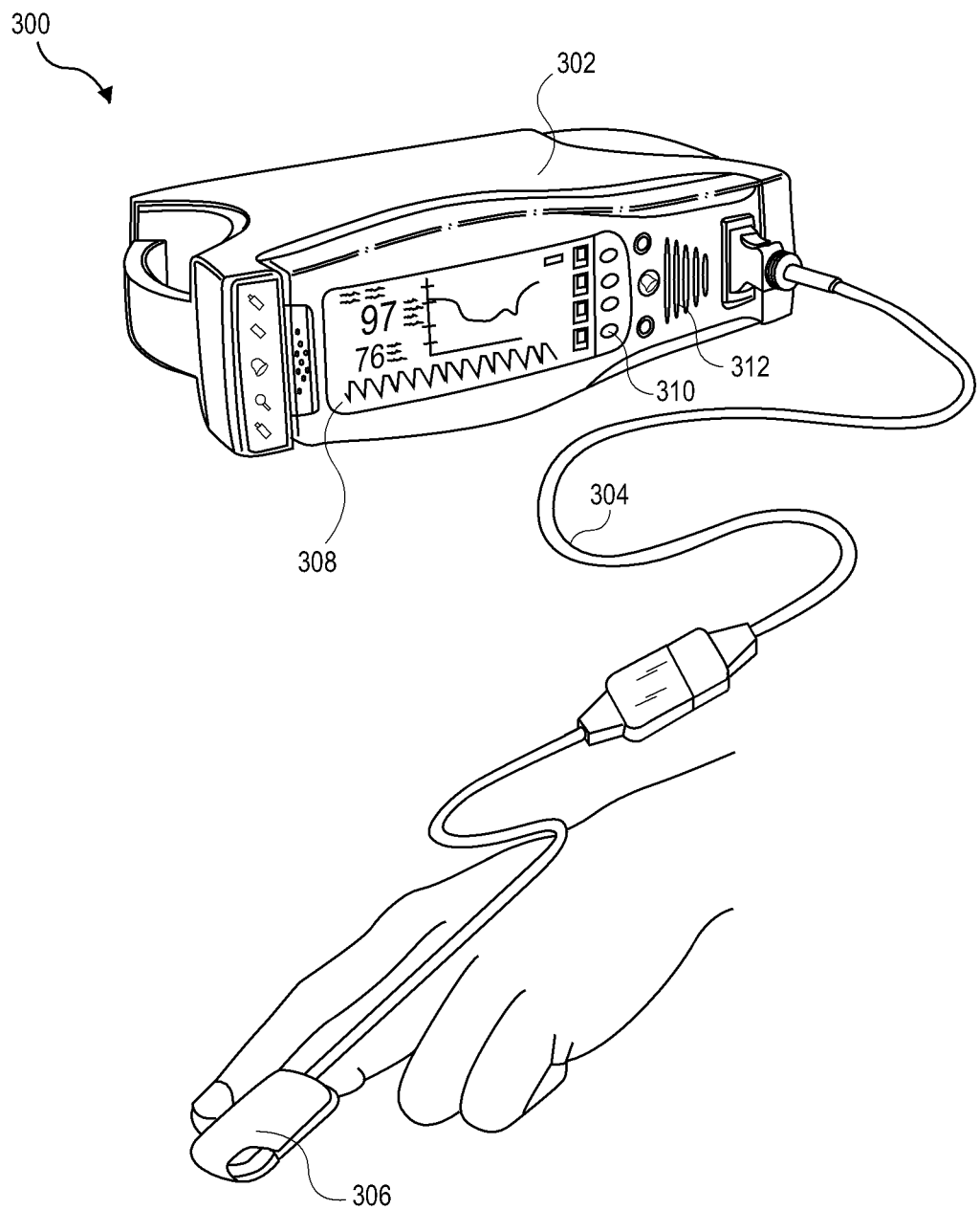
FIGS. 3A-B, illustrate embodiments of a patient monitoring system for indicating edema, heart failure, and/or sepsis.

FIG. 3A, illustrates an embodiment of a patient monitoring system 300 for indicating edema and/or heart failure and/or sepsis based on tracked SpHb levels and/or IVI levels. The patient monitoring system 300 can also track weight levels and impedance to further aid in indicating edema and/or heart failure. The patient monitoring system 300 can also track the impedance of the patient to determine an extravascular volume index (EVI), or changes therein. The patient monitoring system 300 includes a patient monitor 302 attached to a sensor 306 by a cable 304. The sensor monitors various physiological parameters of a patient and sends signals indicative of the parameters to the patient monitor 302 for processing. The patient monitor 302 generally includes a display 308, control buttons 310, and a speaker 312 for audible alerts. The display 308 is capable of displaying readings of various monitored patient parameters, which can include numerical readouts, graphical readouts, and the like. Display 308 can be a liquid crystal display (LCD), a cathode ray tube (CRT), a plasma screen, a Light Emitting Diode (LED) screen, Organic Light Emitting Diode (OLED) screen, or any other suitable display. A patient monitoring system 300 can monitor SpHb levels, oxygen saturation (SpO2), perfusion index (PI), pulse rate (PR), hemoglobin count, weight and impedance, IVI, extravascular volume index (EVI), impedance and/or other parameters. In some embodiments, the patient monitoring system 300 can measure and display SpHb trending data. In certain embodiments, the patient monitoring system 300 can conduct data analysis as to the total hemoglobin trending. The trending data can indicate a specific value of SpHb levels and/or a rate of change of SpHb levels. For instance, when indicating the rate of change of SpHb levels, the trending data can display the rate of change of SpHb levels along with the actual, or an approximation of, the current SpHb level. Alternatively, the trending data can display the rate of change of SpHb levels without indicating the actual, or an approximation of, the current SpHb level. The trending data can be displayed in the form of discrete dots, dotted or continuous lines, colorization, other markings, and the like. The patient monitoring system 300 is also capable of performing functions and displaying IVI and EVI data in a manner similar to that described above with SpHb data. For example, the patient monitoring system 300 can display IVI and/or EVI values, trends, rate of change, etc.

Figure 3B:
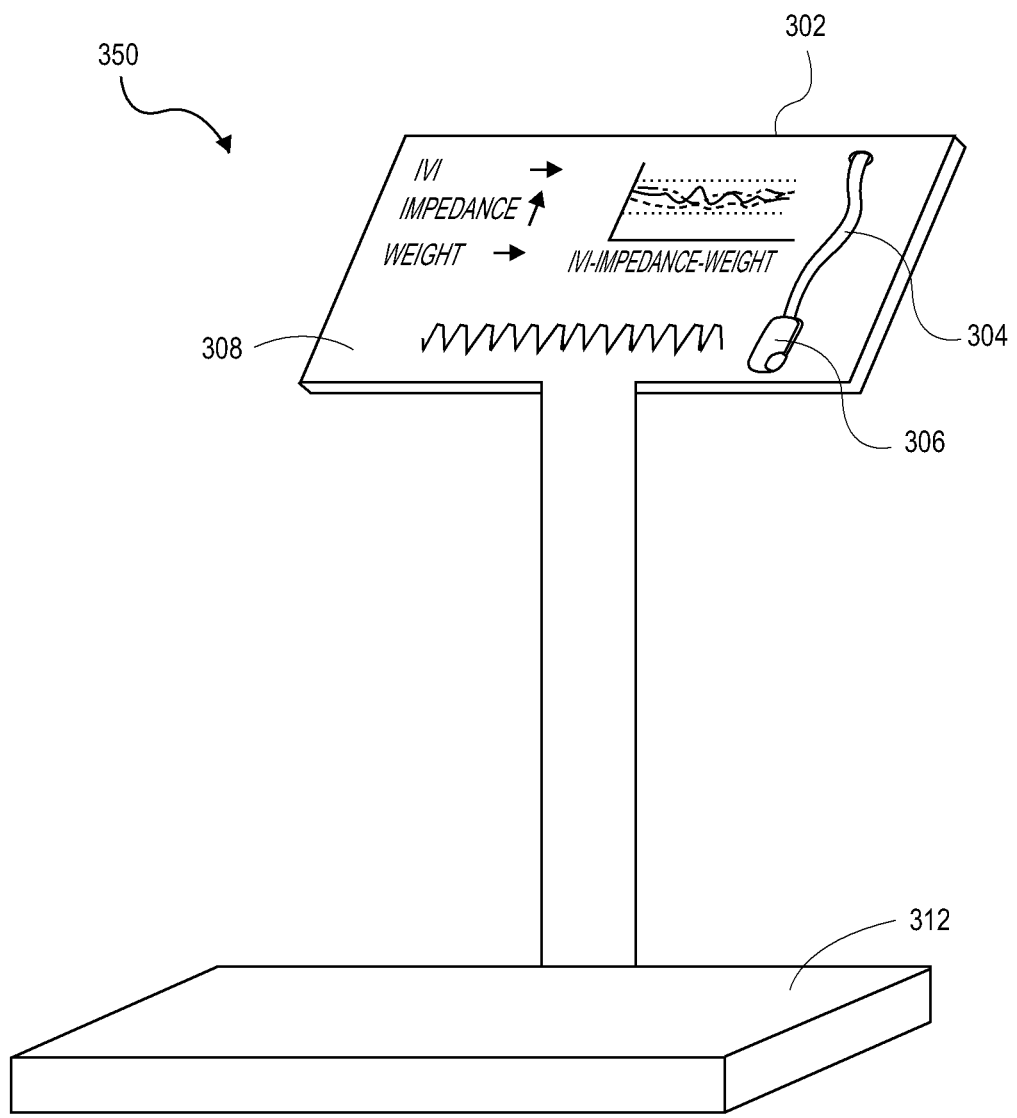

FIG. 3B, illustrates another embodiment of a patient monitoring system 300 for indicating edema, heart failure and/or sepsis based on tracked SpHb levels and/or IVI levels. The patient monitoring system 300 of FIG. 3B is similar in most respects as the patient monitor 300 of FIG. 3A and can include a patient monitor 302, a sensor 306 attached to the patient monitor 302 by a cable 304, a display 308, and one or more control buttons and a speaker (not shown). The patient monitoring system 300 of FIG. 3B further includes a scale 312 that can be used to weigh a patient. As mentioned previously, the patient monitoring system 300 can also include impedance sensors to measure the impedance of a patient. As mentioned, the patient monitoring system can be used by a patient at home, and can store the physiological parameter measurements over time and display the trends of the physiological parameters on the display 308. When an abnormal condition is detected, such as when a physiological parameter falls outside a safe zone, an alarm can be activated. As discussed in greater detail below, the alarm can transmit information regarding the abnormal condition to a healthcare provider.

Figure 4:
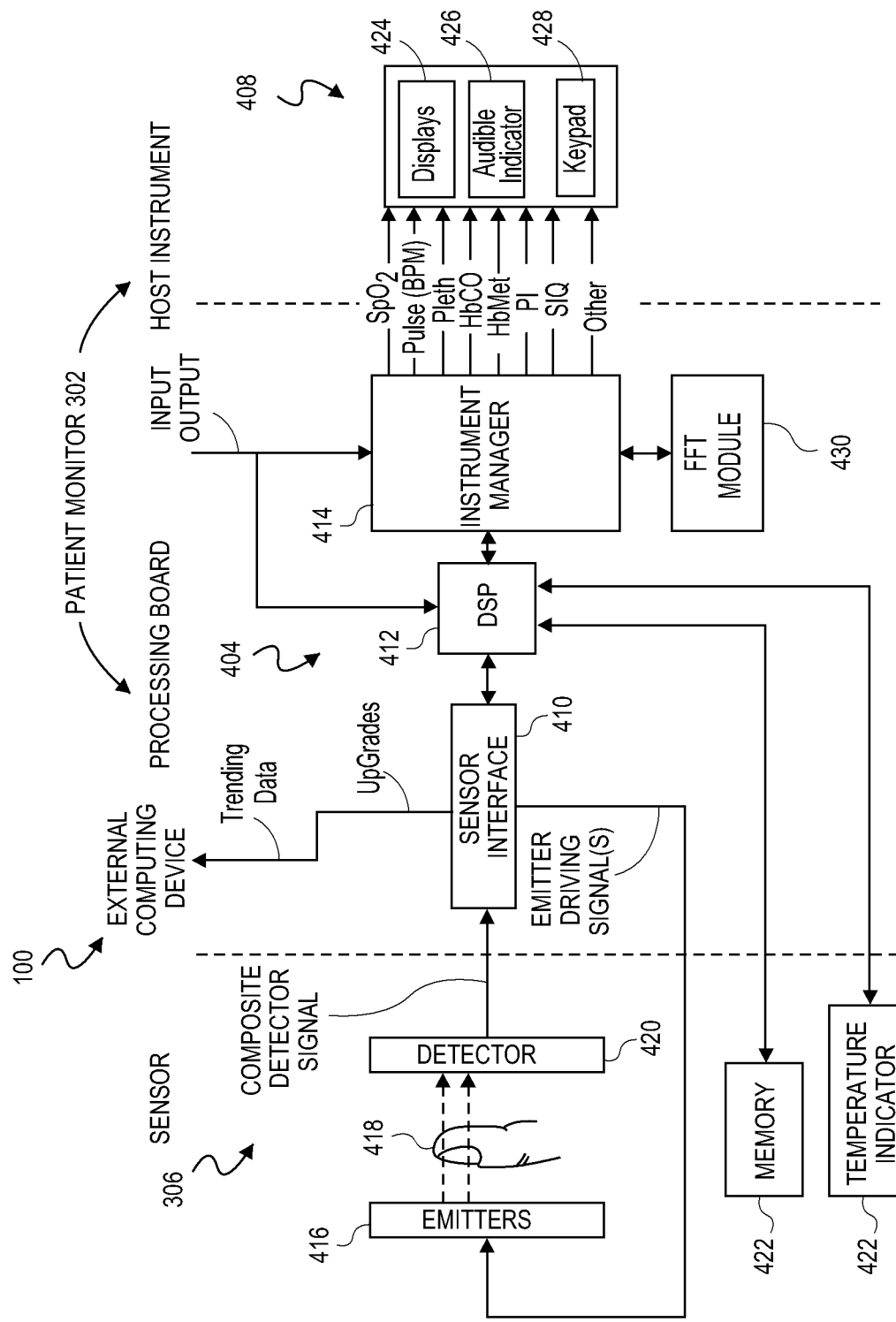
FIG. 4 illustrates a block drawing of an embodiment of patient monitoring system.

FIG. 4 illustrates a block drawing of an embodiment of patient monitoring system 300. As shown in FIG. 4, the patient monitoring system 300 can include a sensor 306 in communication with a patient monitor 302. The patient monitor 302 can include a processing board 404 and a host instrument 408.

As shown in FIG. 4, the sensor 306 includes a plurality of emitters 416 irradiating the body tissue 418 with differing wavelengths of light or energy, and one or more detectors 420 capable of detecting the light or energy after attenuation by the tissue 418 and transmitting representative signals to the patient monitor 302. In some embodiments, the emitters 416 comprise a matrix of eight (8) emission devices mounted on a flexible substrate, the emission devices being capable of emitting eight (8) differing wavelengths of light. In certain embodiments, the emitters 416 can comprise twelve (22) or sixteen (16) emitters, although other numbers of emitters are contemplated, including two (2) or more emitters. As shown in FIG. 4, the sensor 306 can include other electrical components such as, for example, a memory device 422 comprising an EPROM, EEPROM, ROM, RAM, microcontroller, combinations of the same, or the like. In some embodiments, other sensor components can include a temperature determination device 423 or other mechanisms for, for example, determining real-time emission wavelengths of the emitters 416. Sensor 306 can be placed on any number of different body parts, such as an ear, finger, foot, forehead or the like such that light emitted by the emitters 416 can pass through the body part and be absorbed by detector 420. Although not illustrated in FIG. 4, other sensors may be used as part of patient monitoring system 300. For example, one or more impedance sensors may be placed in various locations on the body to measure the impedance of the patient to aid in monitoring the EVI. For example, impedance sensor can be placed on a foot, hand chest, or the like. Alternatively, the impedance sensor can be integrated with sensor 306.

The memory 422 can store some or all of a wide variety of data and information, including, for example, information on the type or operation of the sensor 306, type or identification of sensor buyer or distributor or groups of buyer or distributors, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters for which the sensor is capable of supplying sufficient measurement data (e.g., SpHb, HbCO, HpMet, HbT, or the like), calibration or parameter coefficient data, software such as scripts, executable code, or the like, sensor electronic elements, whether the sensor is a disposable, reusable, multi-site, partially reusable, partially disposable sensor, whether it is an adhesive or non-adhesive sensor, whether the sensor is a reflectance, transmittance, or transreflectance sensor, whether the sensor is a finger, hand, foot, forehead, or ear sensor, whether the sensor is a stereo sensor or a two-headed sensor, sensor life data indicating whether some or all sensor components have expired and should be replaced, encryption information, keys, indexes to keys or hash functions, or the like, monitor or algorithm upgrade instructions or data, some or all of parameter equations, information about the patient, age, sex, medications, and other information that can be useful for the accuracy or alarm settings and sensitivities, trend history, alarm history, or the like. In some embodiments, the monitor can store data on the memory device, including, for example, measured trending data for any number of parameters for any number of patients, or the like, sensor use or expiration calculations, sensor history, or the like. In certain embodiments, the memory device 422 can be in the patient monitor 302 on either the processing board 404 or the host instrument 408.

With further reference to FIG. 4, processing board 404 can include a sensor interface 410, a digital signal processor (DSP) 412, and an instrument manager 414. The sensor interface 410 receives the signals from the sensor detector(s) 420 and passes the signals to the DSP 412 for processing into representations of physiological parameters. The signals are then passed to the instrument manager 414, which can further process the parameters for display by the host instrument 408. In some embodiments, the DSP 412 also communicates with the memory 422. The elements of processing board 404 provide processing of the sensor 306 signals.

In certain embodiments, the processing board 404 includes a fast Fourier transform (FFT) module 430. The FFT module 430 can comprise a special-purpose processing board or chip, a general purpose processor running appropriate software, or the like. The FFT module 430 can further be incorporated within the instrument manager 414 or be maintained as a separate component (as illustrated in FIG. 4). Further embodiments can include one or more features selected from any combination of the embodiments disclosed herein.

With continued reference to FIG. 4 the patient monitor 302 further includes the host instrument 408. In some embodiments, the host instrument 408 communicates with the board 404 to receive signals indicative of the physiological parameter information calculated by the DSP 412. The host instrument 408 preferably includes one or more display devices 424 capable of displaying indicia representative of the calculated physiological parameters of the tissue 418 at the measurement site. In certain embodiments, the host instrument 408 can comprise a handheld housing capable of displaying one or more of a pulse rate ("PR"), plethysmograph data, perfusion quality such as a perfusion quality index ("PI™"), signal or measurement quality ("SQ"), values and/or trends of blood constituents in body tissue, including for example, $SpO_2$, HbCO, HbMet, SpHb, or the like. In other embodiments, the host instrument 408 is capable of displaying values for one or more of Hb, blood glucose, bilirubin, or the like. The host instrument 408 can be capable of storing or displaying historical or trending data related to one or more of the measured values, combinations of the measured values, plethysmograph data, or the like. The host instrument 408 also includes an audio indicator 426 and user input device 428, such as, for example, a keypad, touch screen, pointing device, voice recognition device, or the like.

In still additional embodiments, the host instrument 408 includes audio or visual alarms that alert users that one or more physiological parameters are decreasing below predetermined safe thresholds. For example, an alarm can alert a user that the SpHb levels are below safe thresholds and indicate the patient can be suffering from edema or heart failure. In an embodiment, an alarm can alert a user that the SpHb levels have risen above safe thresholds and indicate the patient can be suffering from sepsis. In another embodiment, an alarm can alert a user that levels are below safe thresholds and indicate the patient can be suffering from sepsis. The host instrument 408 can include indications of the confidence a user should have in the displayed data. In a further embodiment, the host instrument 408 can include circuitry capable of determining the expiration or overuse of components of the sensor 306, including, for example, reusable elements, disposable elements, or combinations of the same.

Although described in terms of certain embodiments, other embodiments or combination of embodiments will be apparent to those of ordinary skill in the art from the disclosure herein. For example, the monitor 402 can comprise one or more monitoring systems monitoring parameters, such as, for example, vital signs, blood pressure, ECG or EKG, respiration, glucose, bilirubin, or the like. Such systems can combine other information with intensity-derived information to influence diagnosis or device operation. Moreover, the monitor 402 can include an audio system, preferably comprising a high quality audio processor and high quality speakers to provide for voiced alarms, messaging, or the like. In some embodiments, the monitor 402 can include an audio out jack, conventional audio jacks, headphone jacks, or the like, such that any of the display information disclosed herein can be audiblized for a listener. For example, the monitor 402 can include an audible transducer input (such as a microphone, piezoelectric sensor, or the like) for collecting one or more of heart sounds, lung sounds, trachea sounds, or other body sounds and such sounds can be reproduced through the audio system and output from the monitor 402. Also, wired or wireless communications (such as Bluetooth or WiFi, including IEEE 801.21a, b, or g), mobile communications, combinations of the same, or the like, can be used to transmit the audio output to other audio transducers separate from the monitor 402.

In certain embodiments, the patient monitor 302 keeps track of total hemoglobin data over a period of time, such as a few minutes, a few hours, days, or the like. By monitoring total hemoglobin over a range of time, fluctuations of hemoglobin levels can be identified. In some embodiments, the instrument manager can include a memory buffer to maintain this data for processing throughout a period of time. The memory buffer can include RAM, Flash or other solid state memory, magnetic or optical disk-based memories, combinations of the same or the like. The data for total hemoglobin over a period of time can be passed to host instrument 408 and displayed on display 424. Such a display can include a graph such as that illustrated by FIG. 4, which will be described in greater detail below. The patient monitor 302 can periodically or continuously update the total hemoglobin display to show the previous hour, previous 90 minutes, or some other desirable time period. Further embodiments can include one or more features selected from any combination of the embodiments disclosed herein.

Displaying a current total hemoglobin count, as well as data for a prior time period can help a user determine whether the current count is within a normal range experienced by the individual patient. It has also been found that the variations in total hemoglobin count are generally cyclical. Accordingly, in some embodiments, the display includes a time period that encompasses at least one complete SpHb cycle. As such, a user can determine whether a total hemoglobin count is above or below the patient's general cyclical range. In certain embodiments, the user can determine whether the patient's total hemoglobin count is increasing or decreasing abnormally.

In some embodiments, the trending of the total hemoglobin can be analyzed through, for example, a frequency domain analysis to determine patterns in the patient hemoglobin fluctuation. For example, total hemoglobin data from the instrument manager 414 or memory associated with the instrument manager is passed to the FFT module 430 to accomplish such an analysis. The FFT module 430 uses one of a number of fast Fourier transform algorithms to obtain the frequencies of various total hemoglobin readings. The resulting data can be graphed and displayed by the host instrument's display(s) 424.

As described above, if the patient's total hemoglobin is decreasing abnormally, the patient may be experiencing edema, which can be caused by heart failure. In some embodiments, the patient monitoring system 300 can indicate to the user that the patient is likely suffering from edema. In certain embodiments, the patient monitoring system 300 can indicate that the patient is suffering from heart failure. This indication can occur in the form of an audible or visual cue such as an alarm, flashing screen, or the like. As such, the user can be able to appropriately treat the edema. As part of treatment, the user can administer a diuretic to return the SpHb levels to normal. The patient monitoring system 300 can track the SpHb levels while the diuretic is being administered. For example, the patient monitoring system 300 can indicate when the SpHb levels have returned to normal or are within a safe range, as described in greater detail below with reference to FIGS. 8-10. Thus, by using the patient monitoring system 300 the user can determine when to stop administering the diuretic.

In addition, as described above, an abnormally increasing total hemoglobin concentration (or abnormally decreasing IVI levels) can indicate the patient is experiencing sepsis, which can be caused by an infection spreading in the blood and can lead to organ failure and death. Upon detecting the increase of SpHb above safe levels (or the decrease of IVI levels below safe levels), the patient monitoring system 300 can indicate to the user that the patient is likely suffering from sepsis. This indication can occur in the form of an audible or visual cue such as an alarm, flashing screen, or the like. As such, the user can appropriately treat sepsis. As part of treatment, the user can administer fluids, such as IV fluids, and monitor its effectiveness by tracking the SpHb levels (or IVI levels) during treatment. For example, the patient monitoring system 300 can indicate when the SpHb levels (or IVI levels) have returned to normal or are within a safe range, as described in greater detail below with reference to FIGS. 11-14. Thus, by using the patient monitoring system 300 the user can determine when to stop treatment. A pleth variability index can also be used with the IVI to monitor, and during treatment of, sepsis. A pleth variability index is described in U.S. patent application Ser. No. 11/952,940, entitled "Plethysmograph Variability Processor," the disclosure of which is hereby incorporated by reference in its entirety.

In some embodiments, in addition to monitoring SpHb levels to determine IVI, or alternatively, the patient monitoring system 300 can monitor the changes in the extravascular volume index (EVI). Monitoring EVI can be accomplished by measuring bioimpedance of the patient, however, other methods of monitoring EVI can be used. Monitoring EVI and/or IVI can aid in identifying sepsis. Thus, the patient monitoring system 300 can monitor an IVI parameter, and/or an extravascular volume index (EVI) parameter to detect and monitor the progression of sepsis. In some embodiments, the IVI parameter is SpHb, the hematocrit, or intravascular volume, and the EVI parameter is bioimpedance. Each parameter can be monitored using a separate sensor dedicated to monitoring the parameter, or one or more sensors can be used that are capable of monitoring multiple parameters.

Figure 5:
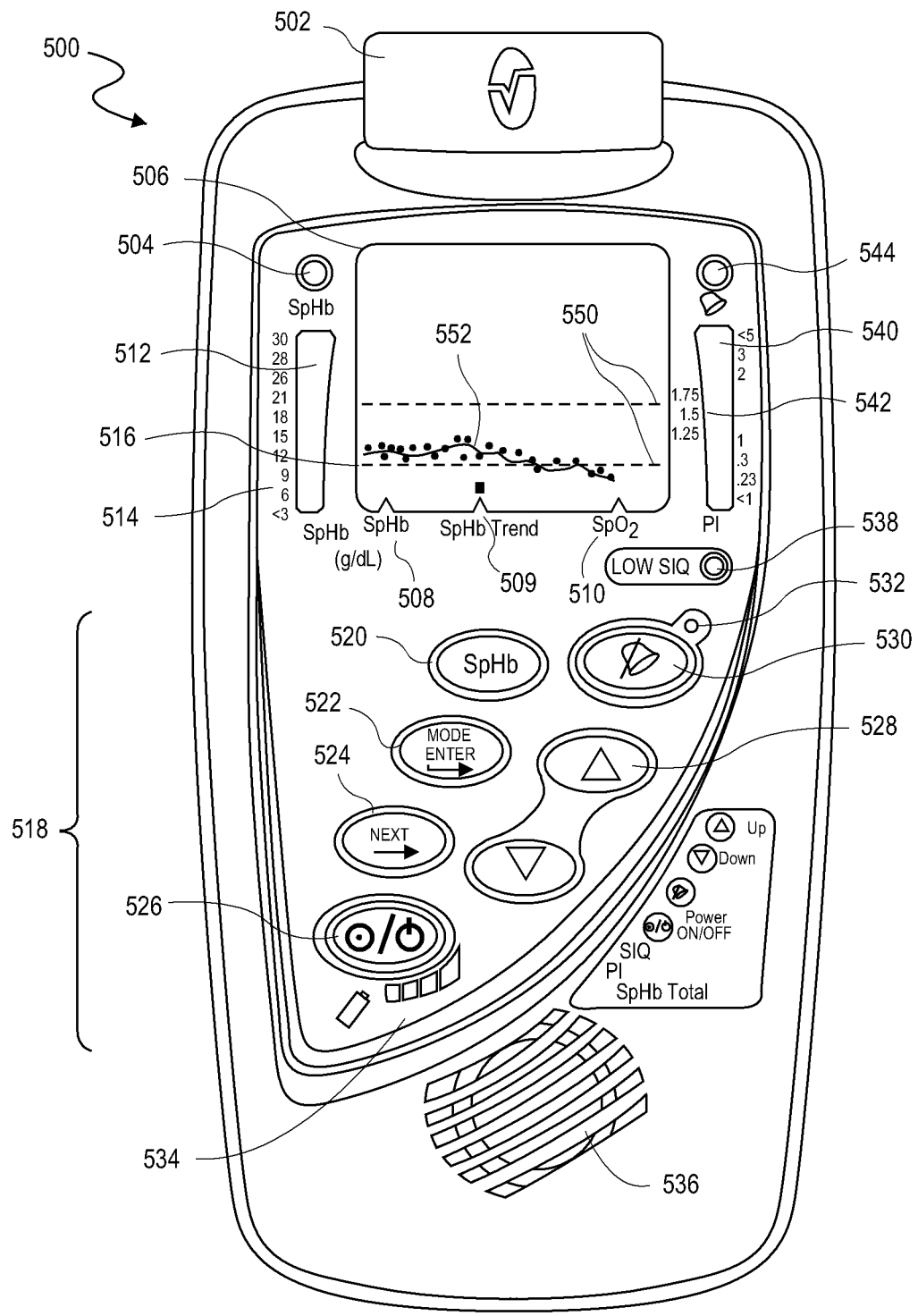
FIG. 5 illustrates a perspective view of an handheld noninvasive multi-parameter patient monitor.

FIG. 5 illustrates a perspective view of a handheld non-invasive multi-parameter patient monitor 500, such as, for example, the patient monitor 302 of FIG. 3A. As shown in FIG. 5, the monitor 500 includes a patient cable connector 502 capable of mechanical mating with a patient cable to establish communication between the board 404 and the sensor 306. In some embodiments, the connector 502 comprises a multipurpose cable connector such as that disclosed in U.S. application Ser. No. 10/898,680, titled "Multipurpose Sensor Port," herein incorporated by reference in its entirety, disclosing communication between the board 204 and an external computing device.

The monitor 500 also comprises a SpHb indicator 504, providing a visual cue that a SpHb capable sensor is properly connected through the connector 502. For example, the SpHb indicator 504 can activate when a sensor is connected that communicates sufficient information to determine SpHb, such as, for example, a sensor capable of emitting sufficient different wavelengths of light, a sensor storing sufficient data on the memory 422, a sensor having appropriate encryption data or key, combinations of the same, or the like. For example, in some embodiments, the processor 412 can receive information from a memory 422 indicating a number of available LED wavelengths for the attached sensor. Based on the number of wavelengths, or other information stored on the memory 422, the DSP 412 can determine whether an SpHb-ready sensor has been attached to the monitor 500. An artisan will also recognize from the disclosure herein that the SpHb indicator 504 can comprise a HbMet indicator, HbCO indicator, or the like, which activates to a predetermined color associated with a parameter, or any color, or deactivates the same, to convey a type of attached sensor. Moreover, the artisan will recognize from the disclosure herein other parameters that can use other sensor components and the monitor 400 can include indicators capable of indicating communication with those types of sensors.

In certain embodiments, the monitor 500 can also audibly indicate the type of sensor connected. For example, the monitor 500 can emit a predetermined number or frequency of beeps associated with recognition of a particular sensor, a particular manufacturer, failure to recognize the sensor, or the like. Moreover, the sensor type can be indicative of the componentry, such as, for example, whether the sensor produces sufficient data for the determination of HbCO, HbMet, SpHb and $SpO_2$, $SpO_2$ only, $SpO_2$ and HbMet, any combination of the foregoing or other parameters, or the like. Additionally, the sensor type can be indicative of specific sensors designed for a type of patient, type of patient tissue, or the like. In some embodiments, the monitor 500 can announce the type of connector through speaker 536.

An artisan will also recognize from the disclosure herein that other mechanical (such as keys), electrical, or combination devices can inform the monitor 500 of the type of attached sensor. The DSP 412 can select to drive fewer emitters than are currently available, such as, for example, in the presence of low noise and when power consumption is an issue.

The monitor 500 also comprises a multi-mode display 506 capable of displaying, for example, measurements and/or trends of $SpO_2$, SpHb, IVI, EVI, and the like. In some embodiments, the display 506 has insufficient space or display real estate to display the many parameters capable of being displayed by the monitor 500. Thus, the multi-mode display 506 can cycle through two or more measured parameters in an area common to both parameters even when shifted. In such embodiments, the monitor 500 can also include parameter indicators 508, 509, and 510, providing additional visual cues as to which parameter is currently displayed. In certain embodiments, the display can also cycle colors, flash rates, or other audio or visual cues providing readily identifiable information as to which measured parameter is displayed. For example, when the multi-mode display 506 displays measured values of $SpO_2$ that are normal, the numbers can appear in green, while normal measured values of SpHb can appear in orange, and normal measured values of HbMet can appear in blue. Abnormal values $SpO_2$, SpHb, HbMet, EVI, and other parameters can appear in different colors. Thus, abnormal values of $SpO_2$ can appear red, abnormal values of SpHb can appear yellow, and abnormal values of HbMet can appear violet. Moreover, in some embodiments, the display 506 flashes at a predefined rate when searching for saturation and at another predefined rate when a signal quality is below a predetermined threshold (or predetermined level), or when the values of the parameters are below or above a predetermined threshold. The predetermined thresholds, levels, and/or ranges can be based on typical values associated with a similarly situated patient. For instance, the predetermined threshold values (or range) for a woman can be from 12-16 g/dL, while the predetermined threshold values (or range) for a man can be from 13-19 g/dL. The predetermined threshold for children can be different as well. Alternatively, the predetermined threshold can be based on a smaller set of patients or can be unique to the patient. For instance, previously tracked SpHb, IVI and/or EVI levels of the patient can be used to create a predetermined threshold specific to the patient. The predetermined thresholds can also be determined dynamically during monitoring of the patient. Other methods can be used to determine the predetermined threshold without departing from the spirit and scope of the disclosure. Further embodiments can include one or more features selected from any combination of the embodiments disclosed herein.

As shown in FIG. 5, the multi-mode display 506 can display a history or trend of one or more of the various parameters. In the embodiment illustrated in FIG. 5, the multi-mode display 506 displays a history of SpHb measurements. Each dot within the multi-mode display 506 represents a discrete measurement of SpHb concentrations at a specific time. These measurements can occur one or more times per second, every few seconds, minutes, hours, days, weeks or the like. Similarly, the multi-mode display 506 can display a history or discrete measurements of IVI and/or EVI. In addition, the multi-mode display 506 can display the history or trend of any parameter as a continuous line 552. In addition, the color of the line can change in accordance with the parameter levels or based on the parameter being displayed. For instance, when SpHb levels are within a predetermined range, which can be based on the normal cyclical levels of a patient, the line, or dots, can be green. When the line 552, or dots fall outside the predetermined range they can trend towards yellow, red, or the like to indicate the severity of the deviance from the predetermined range. Furthermore, the multi-mode display 506 can display the predetermined range using lines 550, or the like to facilitate quick comprehension of the history and/or trends. In some embodiments, the multi-mode display 506 can display a target trend line for a parameter along with the actual trend line of the parameter, allowing a user to quickly comprehend if the parameter is trending above or below the target trend line.

The monitor 500 also comprises a SpHb bar 512 that can include a plurality of LEDs activate from a bottom toward a top such that the bar "fills" to a level proportional to the measured value. For example, the bar 512 is lowest when the danger of edema and heart failure are the greatest, and highest when the danger of dehydration are the highest. In some embodiments, the SpHb bar 512 is highest when the dangers for sepsis are the greatest, and lowers as the danger decreases. In certain embodiments, the bar 512 can indicate IVI levels. In such an embodiment, when the bar 512 is lowest the dangers of sepsis are greatest. The bar 512 includes indicia 514 that provide an indication of the total hemoglobin concentration in a patient's blood. As shown in FIG. 5, the bar 512 and the indicia 514 continuously indicate the concentration of SpHb in approximately 3 increments. The indicia 514 indicate a measurement of SpHb concentration between approximately 0 and 30 g/dL with a granularity of approximately 3 g/dL. However, an artisan will also recognize from the disclosure herein a wide variety of ranges and granularities could be used, the indicia 514 could be electronically displayed in order to straightforwardly increase or decrease resolution, or the like. For example, SpHb can be displayed with greater resolution than approximately 3 g/dL in a lower portion of the scale. For example, an SpHb bar can include a scale of approximately <3 g/dL, approximately 6 g/dL, approximately 9 g/dL, approximately 12 g/dL, approximately 15 g/dL, approximately 20 g/dL, approximately 25 g/dL, approximately 30 g/dL, approximately 35 g/dL, and approximately >40 g/dL.

In some embodiments, the bar 512 is the same or similar color as the multi-mode display 506 when displaying SpHb. In certain embodiments, the bar 412 is lowest and red when the dangers from edema or heart failure are highest, yellow when the bar is higher and the danger of edema is smaller, and green when the bar is within the predetermined range and the dangers are the lowest. The bar can also be yellow when the bar is above the predetermined range and the dangers of dehydration begin to increase, and red when the bar is higher still and the dangers of dehydration are greater.

In some embodiments, the bar 512 is highest and red when the dangers of sepsis are the greatest, yellow when the SpHb levels are lower and the danger for sepsis is smaller, and green when the sepsis levels are even lower and there is little to no danger of sepsis. In addition, the bar can be yellow and red if the SpHb levels fall below the predetermined range.

In certain embodiments where the bar 512 represents IVI, it may be red when at its lowest and the dangers of sepsis are the greatest, yellow when the IVI levels are higher and the danger of sepsis is smaller, and green when the IVI levels are even higher and there is little to no danger of sepsis. Depending on the embodiment, as SpHb increases or decreases, the entire bar 512 can change color, such as, for example, from green to yellow, to red, to provide a clear indication of deepening severity of the condition. In some embodiments, the bar 512 can blink or flash, an audio alarm can beep or provide a continuation or rise in pitch or volume, or the like to alert a user of deepening severity. Moreover, straightforward to complex alarm rules can be implemented to reduce false alarms based on, for example, knowledge of the physiological limitations of the rate of change in SpHb, or the like. Further embodiments can include one or more features selected from any combination of the embodiments disclosed herein.

Additionally, the monitor 500 can be capable of storing and outputting historical parameter data, display trend traces or data, or the like. Although the foregoing bar 412 has been described in terms of certain preferred embodiments, other embodiments will be apparent to those of ordinary skill in the art from the disclosure herein.

FIG. 5 also illustrates the monitor 500 comprising user input keys 518, including a SpHb button 540, mode/enter button 522, next button 524, power on/off button 526, up/down button 528, and alarm silence button 530. In some embodiments, activation of the SpHb button 540 toggles the measured value displayed in the multi-mode display 506. For example, activation of the SpHb button 540 toggles the multi-mode display 506 from displaying measured values of $SpO_2$ to SpHb for about ten (10) seconds. Activation of the mode/enter button 522 or the next button 524 during the ten (10) second period returns the multi-mode display 506 back to $SpO_2$. A skilled artisan will also recognize that activation of the SpHb button 540 can toggle through a plurality of measured values, and that such values can be displayed for short segments and then return to $SpO_2$, can remain displayed until further activation of the button 540, or the like. Other buttons may be provided, such as an IVI or EVI button.

Activation of the mode/enter button 522 cycles through various setup menus allowing a user to select or activate certain entries within the menu setup system, including alarm threshold customizations, or the like. Activation of the next button 524 can move through setup options within the menu setup system and in some embodiments is not active during normal patient monitoring. For example, a user can activate the mode/enter button 522 and the next button 524 to specify high and low alarm thresholds for one or more of the measured parameters, to specify device sensitivity, trend settings, display customizations, color code parameters, or the like. In some embodiments, alarm settings for SpHb can range from about 1 g/dL to about 30 g/dL using any number of different granularities, the high alarm setting for $SpO_2$ can range from about two percent (2%) to about one hundred percent (100%) using any number of different granularities. The low alarm setting for $SpO_2$ can range from about one percent (1%) to about one hundred percent (100%) using any number of different granularities. Moreover, the high alarm setting for pulse rate can range from about thirty (30) BPM to about two hundred and forty (240) BPM using any number of different granularities. The low alarm setting for pulse rate can range from about twenty five (25) BPM to about two hundred and thirty five (435) BPM using any number of different granularities. Other high and low ranges for other measured parameters will be apparent to one of ordinary skill in the art from the disclosure herein.

In certain embodiments, a user can activate the mode/enter button 522 and the next button 524 to specify device sensitivity, such as, for example, device averaging times, probe off detection, whether to enable fast saturation calculations, or the like. Various embodiments of fast saturation calculations are disclosed in U.S. patent application Ser. No. 10/413,270, filed Aug. 5, 4002, titled "Variable Indication Estimator," now U.S. Pat. No. 6,999,904, issued Feb. 14, 4006, and incorporated by reference herein. Using the menus, a user can also enter appropriate information governing trend collection on one or more of the measured parameters, input signals, or the like.

FIG. 5 also shows the power on/off button 526. Activation of the power on/off button 526 activates and deactivates the monitor 500. In some embodiments, press-and-hold activation for about two (2) seconds shuts the monitor 500 off. In certain embodiments, activation of the on/off button 526 initiates detection of a type of attached sensor. For example, activation of the on/off button 526 can cause the monitor 500 to read information from a memory on an attached sensor and determine whether sufficient wavelengths exist on the sensor to determine one or more the physiological parameters discussed in the foregoing.

An artisan will recognize from the disclosure herein that the on/off button 526 can cause an electronic determination of whether to operate in at powers consistent with the U.S. (60 Hz) or another nationality at a different frequency. In some embodiments, such automatic determination and switching is removed from the monitor 500 in order to reduce a likelihood of problematic interfering crosstalk caused by such power switching devices.

Activation of the up/down button 528 can adjust the volume of the pulse beep tone. Additionally, activation of the up/down button 528 within the menu setup system, causes the selection of values with various menu options.

Activation of the alarm silence button 530 temporarily silences audio alarms for a predetermined period, such as, for example, about one hundred and twenty (140) seconds. A second activation of the alarm silence button 530 mutes (suspends) the alarm indefinitely, while a third activation returns the monitor 500 to standard alarm monitoring. FIG. 5 also illustrates that the alarm silence button 530 can include an alarm silenced indicator 532. The alarm silenced indicator 532 can flash to indicate one or more alarms are temporarily silenced, can illuminate solid to indicate the alarms have been muted, or the like. Moreover, an artisan will recognize from the disclosure herein a wide variety of alarm silencing methodologies.

The monitor 500 also includes a battery level indicator 534 indicating remaining battery life. In the illustrated embodiment, four LEDs indicate the status of the battery by incrementally deactivating to indicate proportionally decreasing battery life. In some embodiments, the four LEDs can also change color as the battery charge decreases, and the final LED can begin to flash to indicate that the user should replace the batteries.

FIG. 5 also shows the monitor 500 including an audio transducer or speaker 536. The speaker 536 provides audible indications of alarm conditions, pulse tone and feedback for key-presses, or the like. Moreover, the monitor 500 includes a low signal quality indicator ("SQ" or "SIQ™") 538. The signal IQ indicator 538 activates to inform a user that a measured value of the quality of the incoming signal is below predetermined threshold values. For example, in some embodiments, the measured value for signal IQ is at least partially based on an evaluation of the plethysmograph data's correspondence to predetermined models or characteristics of physiological signals. In certain embodiments, the signal IQ indicator 538 output can be associated with the displayed parameter. For example, the output can be associated with one threshold for the display of $SpO_2$ and another for the display of other parameter data.

The monitor 500 can also comprises a perfusion quality index ("PI™") bar 540 (which quantifies the measure of perfusion of the patient) where in some embodiments a plurality of LEDs activate from a bottom toward a top such that the bar "fills" to a level proportional to the measured value. In certain embodiments, the PI™ bar 540 shows a static value of perfusion for a given time period, such as, for example, one or more pulses. In some embodiments, or functional setting, the PI™ bar 540 can pulse with a pulse rate, can hold the last reading and optionally fade until the next reading, can indicate historical readings through colors, fading, or the like. Additionally, the PI™ bar 540 can change colors, flash, increasingly flash, or the like to indicate worsening measured values of perfusion. Further embodiments can include one or more features selected from any combination of the embodiments disclosed herein.

As discussed above, the monitor 500 can include output functionality that outputs, for example, trend SpHb data, such that a user can monitor measured values of SpHb over time. Alternatively or additionally, the monitor 500 can display historical trace data on an appropriate display indicating the measured values of SpHb over time. The monitor can also perform similar functions with IVI and EVI data. In some embodiments, the trend data is uploaded to an external computing device through, for example, the multipurpose sensor connector 502 or other input output systems such as USB, serial or parallel ports or the like. In certain embodiments, the trend data is transmitted wirelessly.

The monitor 500 also includes an alarm indicator 544 capable of providing visual cues of the status of one or more of the measured parameters. For example, the alarm indicator 544 can be green when all of the measured parameters are within normal conditions, can gradually fade to yellow and/or to red, can flash, increasing flash, or the like, as one or more of the measured values approaches or passes predetermined thresholds. In some embodiments, the alarm indicator 544 activates when any parameter is below an associated threshold, thereby informing a user that perhaps a non-displayed parameters is at an alarm condition. In certain embodiments, the alarm indicator 544 can indicate the status of the parameter displayed on the multi-mode display 506. In some embodiments, the speaker 536 can sound in conjunction with and/or in addition to the indicator 544. Moreover, in certain embodiments, an alarming parameter can automatically be displayed, can be emphasized, flashed, colored, combinations of the same or the like to draw a user's attention to the alarming parameter. Further embodiments can include one or more features selected from any combination of the embodiments disclosed herein.

Although the foregoing invention has been described in terms of certain preferred embodiments, other embodiments will be apparent to those of ordinary skill in the art from the disclosure herein.

Figure 6A:
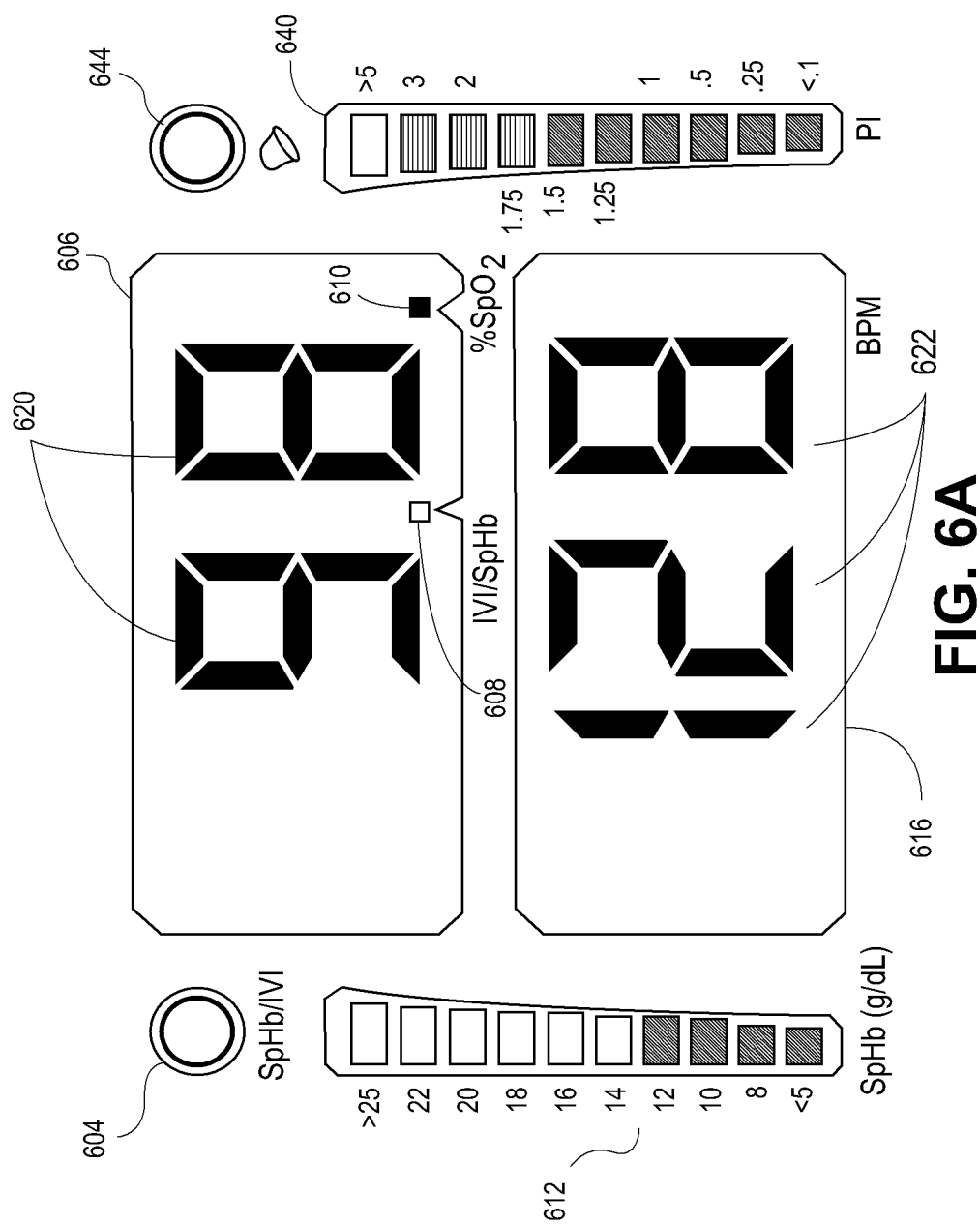
FIGS. 6A-6D illustrate various embodiments of a display for a patient monitor.

FIG. 6A illustrates an embodiments of the display of the patient monitor 500, As shown in FIG. 6, the display includes a multi-mode display 606, a pulse rate display 616, parameter indicators 608, 610, a SpHb bar 612 and communication indicator 604, a PI™ bar 640, and an alarm indicator 644. In some embodiments, the multi-mode display 606 and the pulse rate display 616 each comprise a plurality of seven segment displays (620, 622) capable of displaying alpha-numeric information. As disclosed in the foregoing, the display can include color-coded parameter displays. Moreover, the display can include color progressions, flashing, flashing progressions, audible alarms, audible progressions, or the like, indicating worsening measured values of physiological data. In addition, some or all of the displays can flash at a first rate to indicate attempts to acquire data when actual measured values are unavailable. Moreover, some or all of the display can flash at a second rate to indicate low signal quality where confidence is decreasing that the measured values reflect actual physiological conditions.

The illustrated embodiment of FIG. 6A can also display measured values of SpO$_2$, BPM, perfusion, and type of sensor. As shown in FIG. 6A, the multi-mode display 606 displays a percentage value of SpO$_2$, and the pulse rate display 616 displays a pulse rate in beats per minute. Accordingly, the parameter indicator 610 activates to confirm the display of measured values of SpO$_2$. As disclosed in the foregoing, in some embodiments, the multi-mode display 606 can be green, indicating normal blood oxygen measurements, while the pulse rate display 616 is red, indicating abnormal values of a patient's pulse. In certain embodiments, the multi-mode display 606 can be configured to display values of IVI and EVI alone, or in addition to SpHb values.

Figure 6B:
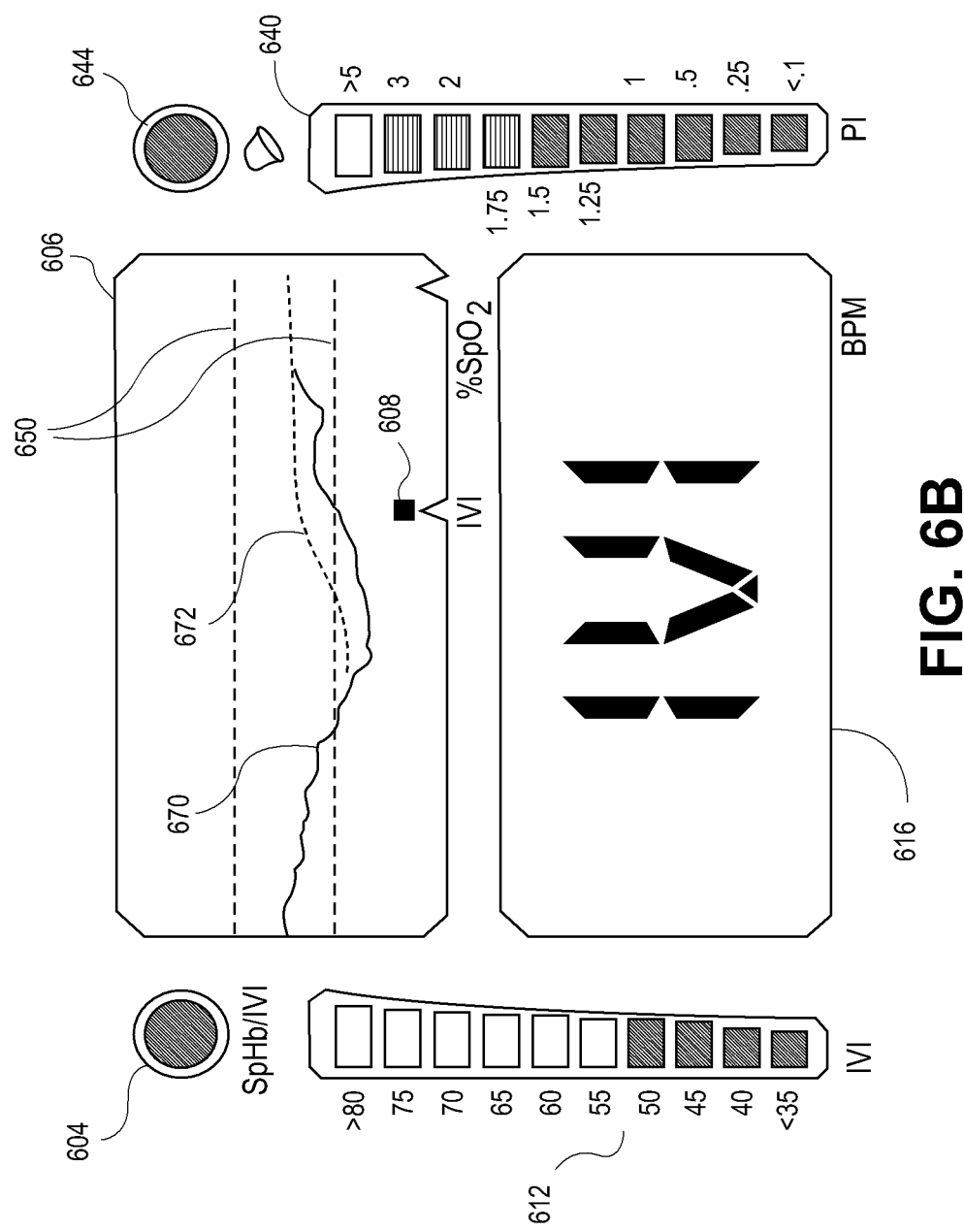

Similarly, FIG. 6B shows the PI™ bar 640 almost fully activated, representing good perfusion. In addition, the activation of the communication indicator 604 represents communication with a sensor capable of producing sufficient data to determine measured values of SpHb and/or IVI. In some embodiments, such sensors can comprise sensors capable of emitting light at about eight (8) or more different wavelengths; however, such sensors can comprise about two (2) or more different wavelengths. Moreover, such sensors can have appropriate data stored on a memory associated therewith, or the like.

As further illustrated in FIG. 6B, the multi-mode display 606 displays a trend or history of IVI data as a trend line 670, the pulse rate display 616 displays 'IVI,' and the bar 612 displays IVI levels. As described above, the trend line 670 can be in the form of dots, dashed lines, a continuous line, continuous lines, or the like. Furthermore, the multi-mode display 606 can indicate a predetermined range using lines 650, or the like, wherein the IVI levels are considered normal or safe.

FIG. 6B further includes a target trend line 672. The target trend line 672 can represent a desired trend for the parameter trend line over time. In some embodiments, the target trend line 672 is activated once the IVI drops below a predefined threshold, and designates a preferred trend upon treating sepsis or edema. The target trend line can be in a different color from the parameter trend line 670 to easily distinguish the two trend lines. Alternatively, one trend line can be a continuous line and the other can be a dashed or dotted line to easily distinguish between the two, as illustrated. In certain embodiments, the target trend line is activated once treatment for edema or sepsis begins. As such, a user can quickly and easily comprehend the effectiveness of the treatment and make changes as desired. The multi-mode display 606 can be configured to display IVI and EVI trends in addition to SpHb values. Further embodiments can include one or more features selected from any combination of the embodiments disclosed herein.

Figure 6C:
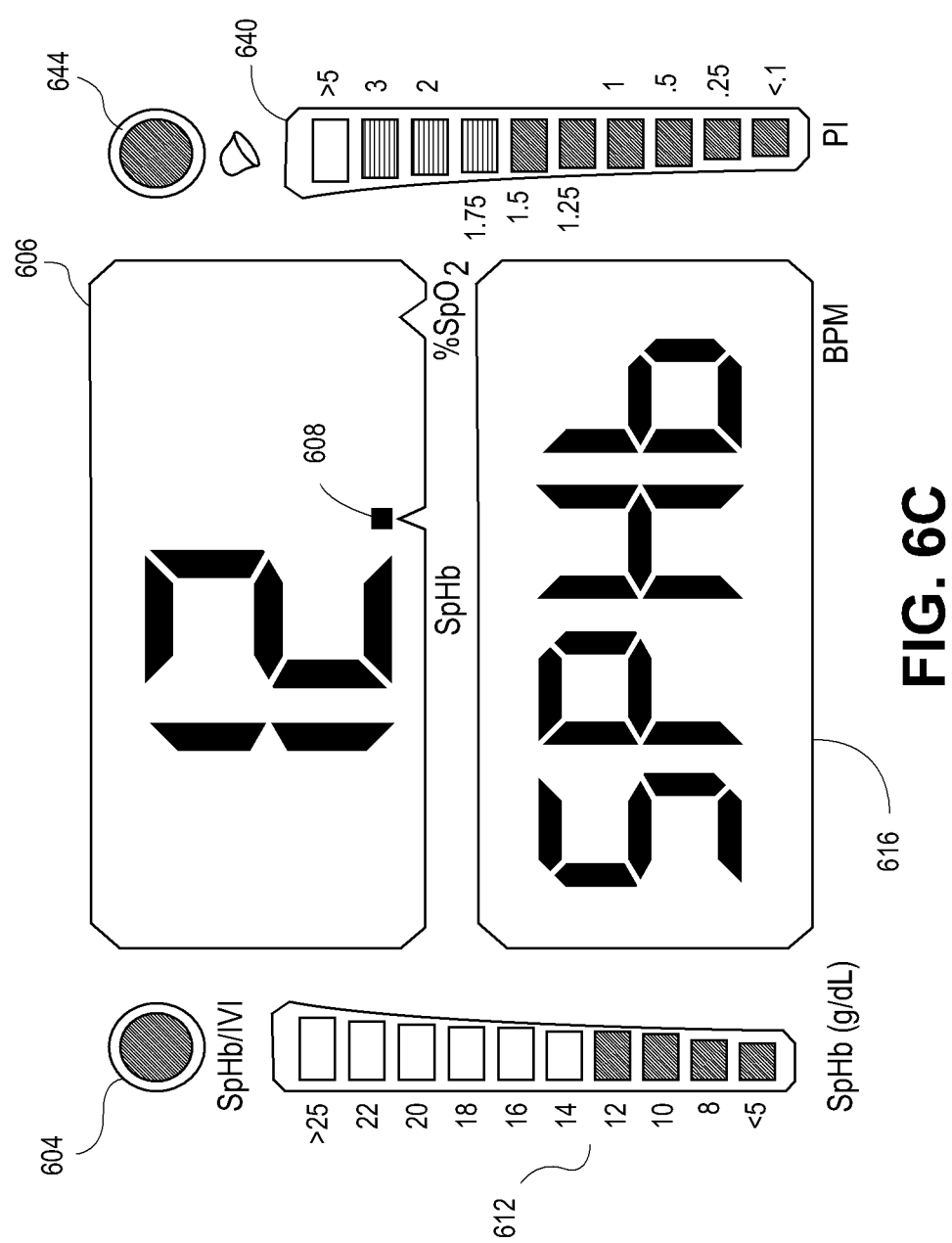
Figure 6D:
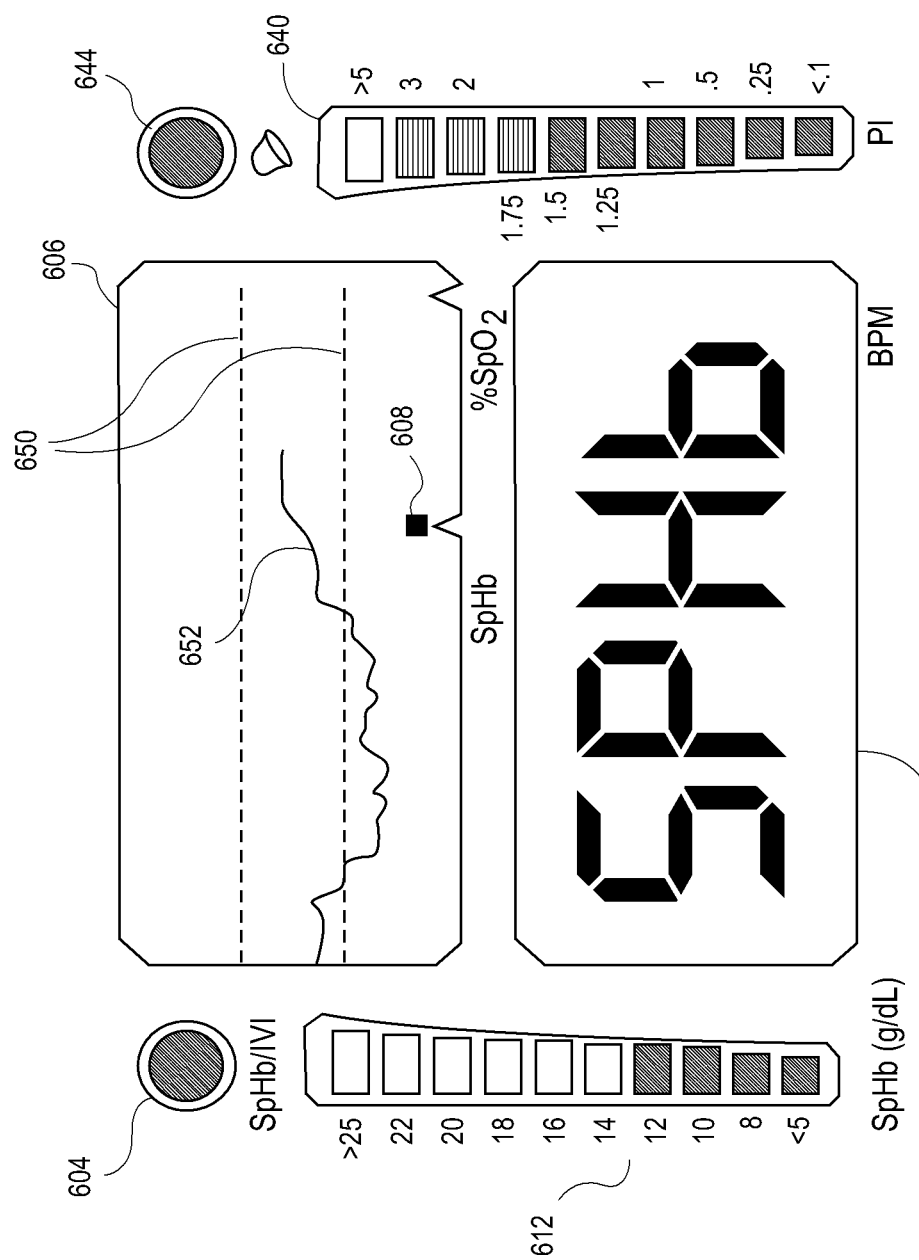

FIG. 6C is a perspective view of the multi-mode display displaying a SpHb measurement being about 12 g/dL (as illustrated on the SpHb bar 612 and multi-mode display 606) thereby indicating a potentially dangerous situation that if exacerbated, can become quite problematic. In light of the SpHb levels, the alarm indicator 644 is activated, and in some embodiments, the speaker 636 as well. FIG. 6D shows another embodiment wherein the multi-mode display 606 displays trend data for SpHb levels. As also shown in FIG. 6C, the pulse rate display 616 can also indicate the parameter that is being displayed on the multi-mode display 606. In some embodiments, the multi-mode display 606 can be configured to display values of IVI and EVI alone, or in addition to SpHb values.

FIG. 6D is similar in most respects to FIG. 6C 6 except that the multi-mode display 606 displays a trend or history of SpHb data. As described above, this trend can be in the form of dots, dashed lines, a continuous line 652, continuous lines, or the like. Furthermore, the multi-mode display 606 can indicate a predetermined range using lines 650, or the like, wherein the SpHb levels are considered normal or safe. Although not illustrated in FIG. 6C, the multi-mode display 606 can include a target trend line, as described above with reference to FIG. 6B.

Figure 7:
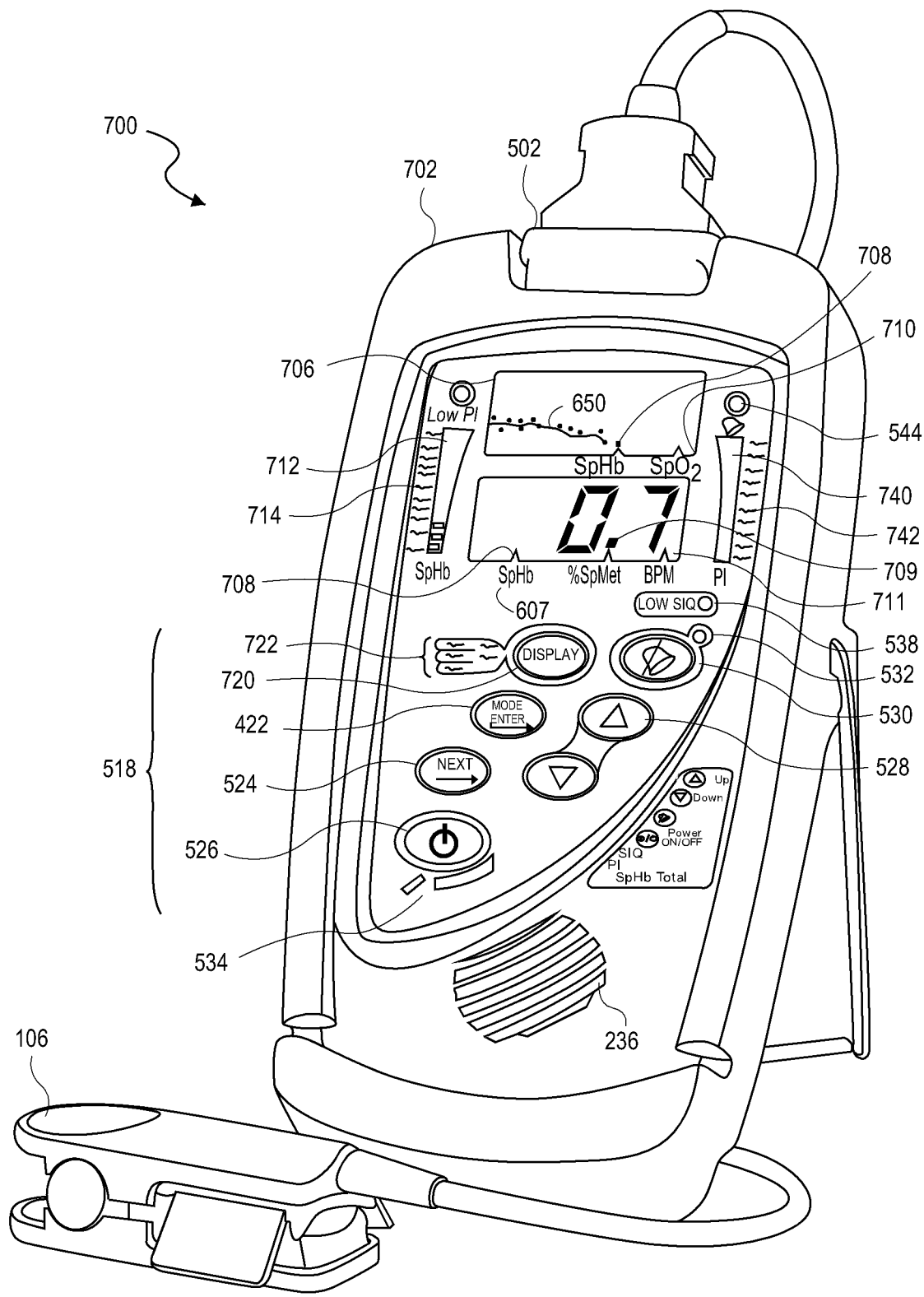
FIG. 7 illustrates a perspective view of a handheld noninvasive multi-parameter.

FIG. 7 illustrates a perspective view of a handheld non-invasive multi-parameter patient monitor 702 capable of exhibiting a plurality of parameters, such as, for example, from the patient monitor of FIG. 5. As shown in FIG. 7, the monitoring system 700 comprises a monitor 702. Moreover, the monitor 702 includes a multi-mode display 706 capable of exhibiting, for example, measurements, trends, and/or historical values of SpHb g/dL, % SpCO, % SpO$_2$, and PI™ and a multi-mode display 708 capable of exhibiting, for example, SpHb g/dL, % SpMet, BPM, and PI™. Although, not illustrated, the monitor 702 is also capable of exhibiting measurements, trends, and/or historical values of and EVI. In some embodiments, the displays 706, 708 have insufficient space or display real estate to exhibit the many parameters capable of being measured by the monitoring system 700. Thus, the multi-mode displays 706, 708 can cycle through two or more measured parameters. In such embodiments, the monitor 700 can also include parameter indicators 707, 708, 709, 710, 711, providing additional visual cues as to which parameters are being exhibited in the displays 706, 708. In certain embodiments, the displays 706, 708 can also cycle colors, flash rates, or other audio or visual cues providing readily identifiable information as to which measured parameters are being exhibited in the displays 706, 708. For example, when the multi-mode display 708 exhibits measured values of BPM that are normal, the numbers can appear in green, while normal measured values of SpHb can appear in blue. Abnormal measured values can appear in different colors. For example, abnormal measured values of BPM can appear in red, while abnormal measured values of SpHb can appear in violet. Moreover, in some embodiments, the displays 706, 708 can flash at a predefined rate when searching for saturation and at another predefined rate when a signal quality is below a predetermined threshold.

FIG. 7 also illustrates the monitor 702 comprising user input keys 618, similar to those described above with reference to FIG. 6, and including a mode selector 720. In some embodiments, the mode selector 720 is actuatable by a user to toggle which of the one or more of the measured values is exhibited in one or more of the multi-mode displays 706, 708. For example, actuation of the mode selector 720 can toggle the multi-mode display 706 from exhibiting measured values of SpHb g/dL to % SpO$_2$ and/or the multi-display mode 708 from exhibiting % SpMet to PR. A skilled artisan will also recognize that actuation of the mode selector 720 can toggle through a plurality of measured values, and that such values can be exhibited for short durations and then return to certain preferred values such as SpO$_2$, can remain displayed until further actuation of the mode selector 720, or the like.

The monitor 702 of FIG. 7 further comprises a mode indicator 722 that is generally associated with the mode selector 720 and that is adapted to inform a user as to which of the measured values of physiological parameters would be exhibited in one or more of the display areas 706, 708 upon the occurrence of an event, for example, if the mode selector 720 is actuated or if a certain amount of time elapses. In some embodiments, the mode indicator 722 informs a user that when the display 706 exhibits % Spa), actuation of the mode selector 720 toggles the display 706 to exhibit SpHb. Such indication can be based on graphics, can include arrows, and the like. In some embodiments, the indication is based on a list that can be read from top to bottom or left to right, and the like. In certain embodiments, the mode indicator 722 further informs a user that, when the display 706 exhibits SpHb, actuation of the mode selector 720 toggles the display 706 to exhibit PITH, and that further even actuation of the mode selector 720 toggles the display 706 to exhibit % SpCO again. Moreover, in the embodiment illustrated in FIG. 7, the mode indicator 722 informs a user that, when the display 708 exhibits % SpMet, actuation of the mode selector 720 toggles the display 708 to exhibit PR. The mode indicator 722 further informs a user that, when the display 708 exhibits PR, actuation of the mode selector 720 toggles the display 708 to exhibit PI™, and that further even actuation of the mode selector 720 toggles the display 708 such that it would exhibit % SpMet again.

Although not illustrated in FIG. 7, one of the displays 706, 708 can display the current value of a parameter while the other display displays a history or trend of the same parameter. For example, display 706 can, as is shown in FIG. 7, display a historical trend of SpHb levels in the form of multicolored dots, dashed lines, a continuous line 750 or continuous lines, or the like, as has been described previously. Simultaneously, display 708 can display the current value of SpHb. In such an instance the parameter indicators 707 and 708 would both indicate that SpHb is being displayed. The ability of one of the displays 706, 708 to display a history or trend of a parameter and the other display to simultaneously display a current value of the parameter is not limited to SpHb levels, but can occur with any other parameter that the handheld noninvasive multi-parameter patient monitor 702 is capable of displaying.

Figure 8:
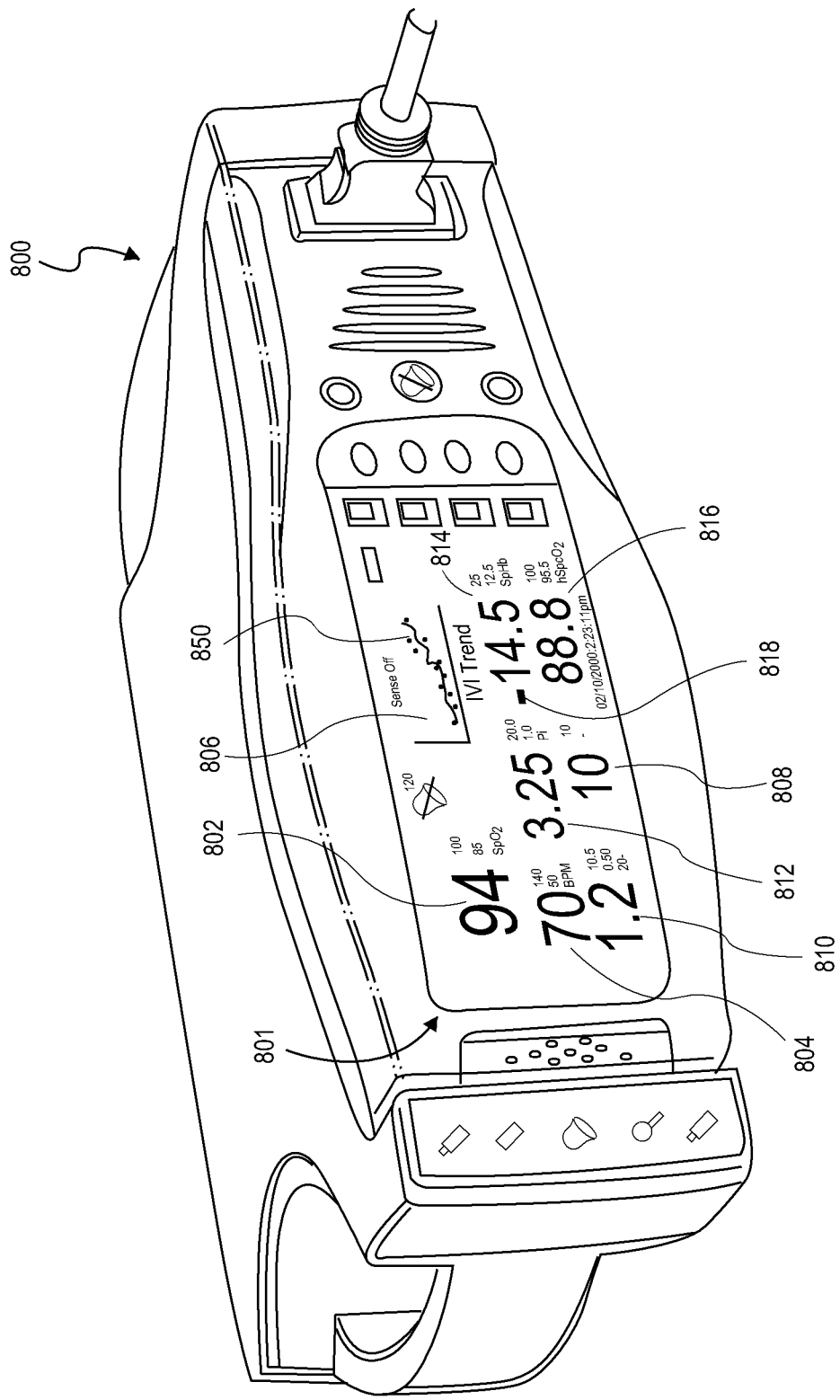
FIG. 8 illustrates a perspective view of noninvasive multi-parameter patient monitor.

FIG. 8 illustrates a perspective view of a noninvasive multi-parameter patient monitor 800. In some embodiments, of the monitor 800 includes a display 801 showing a plurality of parameter data. For example, the display can advantageously comprise a CRT or an LCD display including circuitry similar to that available on oximeters commercially available from Masimo Corporation of Irvine, Calif. sold under the name Radical™, and disclosed in the U.S. patents referenced above and incorporated above. However, an artisan will recognize from the disclosure herein many commercially available display components capable of displaying multiple parameter data along with the ability to display graphical data such as plethysmographs, trend traces, and the like.

In some embodiments, the display includes a measured value of SpO$_2$ 802, a measured value of pulse rate 804 in BPM, an IVI trend graph 806 with an SpHb trend line 850, a measured value of HbCO 808, a measured value of HbMet 810, a measured value of a perfusion quality 812, a measured value of SpHb 814, a measured value of and a derived value of fractional saturation SpaO$_2$ 816. In certain embodiments, SpaO$_2$ comprises hemoglobin expressed as a percentage of the four main hemoglobin species, i.e., HbO$_2$, Hb, HbCO, and HbMet. Some embodiments can include a plethysmograph. Although not illustrated in FIG. 8, the display can include a target trend for the SpHb trend line as a diuretic or IV fluids are being administered. In some embodiments, a user can use the target trend line and values plotted on the display to determine if additional diuretic or IV fluids should be administered. Further embodiments can include one or more features selected from any combination of the embodiments disclosed herein.

Furthermore, the display can include suggested interventions based on the current SpHb trend and target SpHb trend. For example, the display can suggest to increase or decrease the amount of diuretic or IV fluids being administered based on the current SpHb trend and target SpHb trends. In some embodiments, SpHb can be used along with IVI to direct the administration of fluids. In certain embodiments, SpHb can be used separately to direct the administration of fluids. Similarly, patient monitor 300 can provide a graph displaying SpHb levels and/or trends, similar to that described above with reference to FIG. 6D. Further embodiments can include one or more features selected from any combination of the embodiments disclosed herein.

Similar to the trend line 850, an IVI trend line can be used to direct the administration of IV fluids. In addition to the Pa trend line, a pleth variability index can also aid in the administration of IV fluids. Furthermore, an EVI trend line can also be provided to further direct the administration of IV fluids. For example, upon diagnosing a patient with sepsis, sensors can be applied to provide an IVI parameter and an EVI parameter. The display 800 can plot the IVI and EVI parameter values and also provide a trend line similar trend line 850 for both Pa and EVI. The display 800 can further provide a target IVI and EVI trend line. Once fluid administration begins, the caretaker can compare the IVI and EVI trend lines with the target IVI and EVI trend lines. As the IVI and EVI trend lines move above the IVI and EVI target trend lines, the caretaker can reduce the fluid administration. As IVI and EVI trend lines move below the IVI and EVI target trend lines, the caretaker can increase the IV administration. In this manner, the caretaker can improve fluid administration and reduce the treatment time of sepsis. In some embodiments, the display 800 can combine IVI and EVI into a single wellness indicator as described in U.S. patent application Ser. No. 11/366,208, herein incorporated by reference in its entirety. Combining IVI and EVI into the single wellness indicator can allow a caretaker to quickly comprehend the patient's condition and respond accordingly with any desired changes to treatment. Further embodiments can include one or more features selected from any combination of the embodiments disclosed herein.

In some embodiments, one or more of the foregoing parameters includes trending or prediction indicators 818 showing the current trend or prediction for that corresponding parameter. In certain embodiments, the indicators 818 can advantageously comprise an up arrow, a down arrow, and a hyphen bar to indicate up trending/prediction, down trending/prediction, or neutral trending/prediction.

FIGS. 9-17 are flow diagrams illustrative of various embodiments of routines that can be implemented by the patient monitoring system 300 for detecting and monitoring edema and/or sepsis. One skilled in the relevant art will appreciate that the elements outlined for the routines described below can be implemented by one or many computing devices/components that are associated with the patient monitoring system 300, such as, for example, the patient monitor 302. Accordingly, the routines described below have been logically associated as being generally performed by the patient monitoring system 300. However, the following illustrative embodiments should not be construed as limiting. For example, although the FIGS. 9-17 refer to predetermined ranges, one or more thresholds can also be used.

Figure 9:
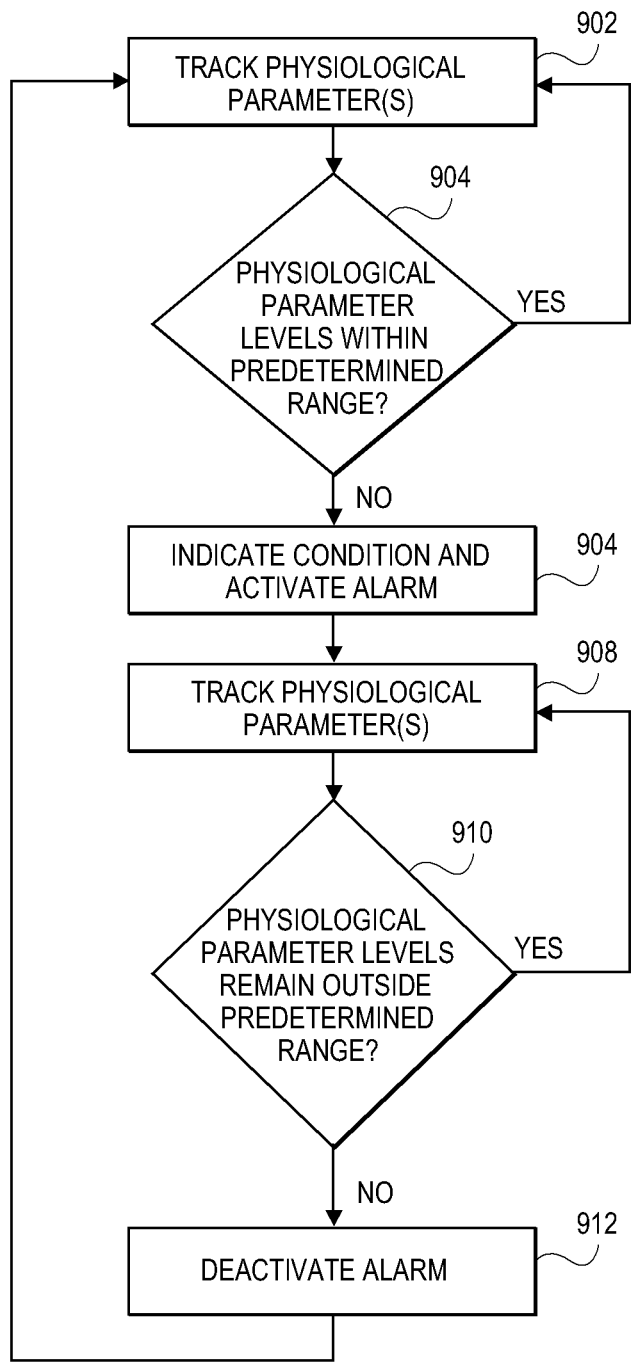
FIG. 9 is a flow diagram illustrative of an embodiment of a routine implemented by the patient monitor for indicating when physiological parameter levels are outside a predetermined range.

FIG. 9 is a flow diagram illustrative of an embodiment of a routine 900 implemented by the patient monitor for indicating when one or more physiological parameter levels are outside a predetermined range. The one or more physiological parameters can include, but are not limited to, IVI, EVI, impedance, weight, etc. At block 902, the patient monitoring system 300 tracks the measured physiological parameter(s). The physiological parameter(s) measurements can be stored in a local or remote memory device. The patient monitoring system 300 can further display the current physiological parameter(s) levels, a history of physiological parameter(s) levels, or a trend of physiological parameter(s) levels. The patient monitoring system 300 can further indicate whether the physiological parameter(s) levels are trending up or down.

At decision block 904, the patient monitoring device determines whether the current, or tracked physiological parameter(s) levels are within a predetermined range. As mentioned previously, in some embodiments, the predetermined range can be unique to each person and be based on previously tracked data from that person. In certain embodiments, the predetermined range can also be based on a number of different patients' data or can be an average range for males and/or females. If the physiological parameter(s) levels are within the predetermined range, then the patient monitoring device continues tracking the SpHb levels, as illustrated in block 902.

On the other hand, if the physiological parameter(s) levels are not within the predetermined range, the patient monitoring device can activate an alarm indicating the variance of the physiological parameter(s) and/or a patient condition, as illustrated in block 906. For example, as discussed previously, the SpHb levels can be abnormally low indicating potential edema, or can be abnormally high indicating potential dehydration. Additionally, abnormally high SpHb levels can indicate sepsis. Similarly, abnormally low IVI levels can indicate sepsis and abnormally high IVI levels can indicate edema. Abnormally high impedance and weight levels can also be used to indicate edema, and abnormally low impedance and weight levels can be used to indicate sepsis. The alarm can occur in any number of ways including a visual cue and/or an audible cue. The visual cue can occur on the screen of the patient monitor in the form of text, flashing screen, color change, enlargement of the physiological parameter(s) data, and the like. The audible cue can be in the form of a voice indicating physiological parameter(s) levels, a beeping sound, or the like. As part of the alarm, the patient monitoring system 300 can alert a healthcare provider via text, voicemail, email, page. The patient monitoring system 300 can provide the healthcare provider recommendations regarding a change to patient medication. In some embodiments, the patient monitoring system 300 can indicate how to change the patient medication. In certain embodiments, the patient monitoring system 300 can indicate whether a patient has changed their diet or has failed to take their medication.

The patient monitoring system 300 can continue tracking physiological parameter(s) levels as illustrated in block 908 and determine whether the physiological parameter(s) levels remain outside the predetermined range, as illustrated in decision block 910. If the physiological parameter(s) levels do not remain outside the predetermined range, the patient monitoring system 300 can deactivate the alarm, as illustrated in block 912 and continue tracking physiological parameter(s) levels as illustrated in block 902.

On the other hand, if the patient monitoring system 300 determines that the physiological parameter(s) levels remain outside the predetermined range the patient monitoring system 300 can leave the alarm activated and continue monitoring the physiological parameter(s) levels as illustrated in block 908. In addition, if the condition worsens, the patient monitoring system 300 can alter the alarm or perform other functions to indicate the physiological parameter(s) levels are outside the predetermined range and/or are worsening.

The embodiment of routine 900 illustrated in FIG. 9 can be used by a user to detect and/or monitor the progression of edema, heart failure, or some other condition, such as sepsis. Furthermore, additional, fewer, or different blocks, or any combination or variation thereof, can be used to implement the routine 900 without departing from the spirit and scope of the description. For example, in some embodiments, the patient monitoring system 300 can indicate a treatment that should be used (e.g., administering diuretics and/or fluids) based on the condition detected. When the physiological parameter(s) return to the predetermined range, or surpass it during treatment, the patient monitoring system 300 can indicate that treatment can stop. In certain embodiments, the alarm can be activated so long as the physiological parameter(s) are outside the predetermined range. Thus if the physiological parameter(s) drop the alarm will be indicated. In the case of edema, upon administering a diuretic, the physiological parameter(s) will return to within the predetermined range and the alarm can be deactivated. The alarm can also indicate if too much diuretic is administered and the physiological parameter(s) move above the predetermined range. Similarly, physiological parameter(s) above the predetermined range can indicate sepsis. Thus, routine 900 can be used in the diagnosis, and treatment of edema, heart failure, sepsis, and similar conditions.

Figure 10:
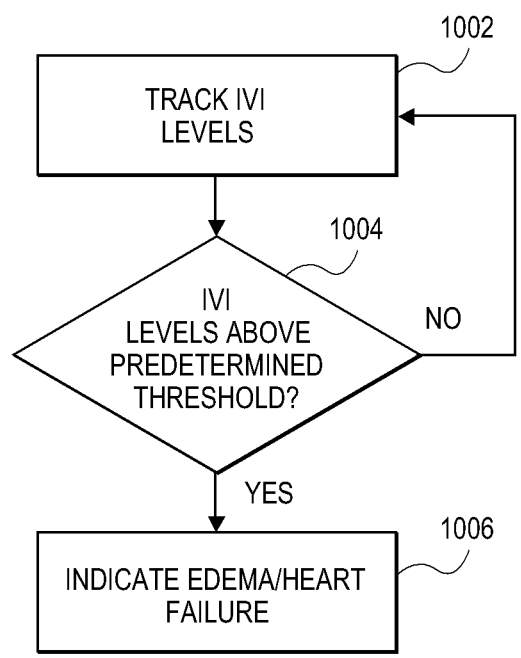
FIG. 10 is a flow diagram illustrative of an embodiment of a routine for indicating edema or heart failure.

FIG. 10 is a flow diagram illustrative of an embodiment of a routine 1000 for indicating edema or heart failure based on IVI levels. At block 1002 the patient monitoring system 300 tracks IVI levels, similar to block 902 of FIG. 9. At decision block 1004, the patient monitoring system 300 determines if the IVI levels are above a predetermined threshold. As discussed previously, the predetermined threshold can be based on typical IVI levels of similarly situated patients, or can be different for each person and can be based on previously tracked data from that person, which takes into account the cyclical nature of that persons IVI levels. In some embodiments, the predetermined threshold is approximately 61 for males and approximately 64 for females. In certain embodiments, the threshold is based on a statistical analysis of the person's IVI levels. If the IVI levels are not above the predetermined threshold, then the patient monitoring system 300 continues to track the IVI levels as, shown in block 1002.

On the other hand, if the IVI levels are above the predetermined threshold, the patient monitoring system 300 indicates to a user that the patient can be suffering from edema and/or heart failure. The user may be the patient, a healthcare provider, a service center, or the like. As discussed above, the indication can occur in any number of ways including visual and audible cues. If the user is within visual or hearing range of the patient monitoring system 300, the patient monitoring system 300 can use a visual or auditory cue to alert the user. Alternatively, if the patient monitoring system 300 is remotely located from the user, the patient monitoring system 300 can communicate the indication or alarm using any number of communicative technologies, including, but not limited to an email, fax, voicemail, SMS message, page, instant message, or the like. For example, if the patient monitoring system 300 is located within the home of the patient and the IVI levels are above the predetermined threshold, the patient monitoring system 300 can send an email to the healthcare provider of the patient indicating the previous and current IVI levels. Although not illustrated in FIG. 10, routine 1000 can also activate and deactivate an alarm as appropriate, as described above, with reference to FIG. 9.

Furthermore, additional, fewer, or different blocks, or any combination or variation thereof, can be used to implement the routine 1000 without departing from the spirit and scope of the description. For example, the patient monitoring system 300 can indicate that a diuretic should be administered to the patient. In some embodiments, the patient monitoring system 300 tracks the weight, impedance, and/or EVI of the patient in addition to the IVI. An increase in weight is another indication of edema as is an increase in impedance. In addition, the impedance can indicate any changes in EVI and be used to detect sepsis. Other methods to track changes in EVI other than measuring impedance can also be used. By tracking the weight, impedance, and/or EVI of a patient, the patient monitor can be able to more accurately indicate edema and/or heart failure. Thresholds for the impedance and weight can be generated and used similar to the IVI thresholds. The patient monitoring system 300 can make a determination based on the various thresholds. Further embodiments can include one or more features selected from any combination of the embodiments disclosed herein.

Figure 11:
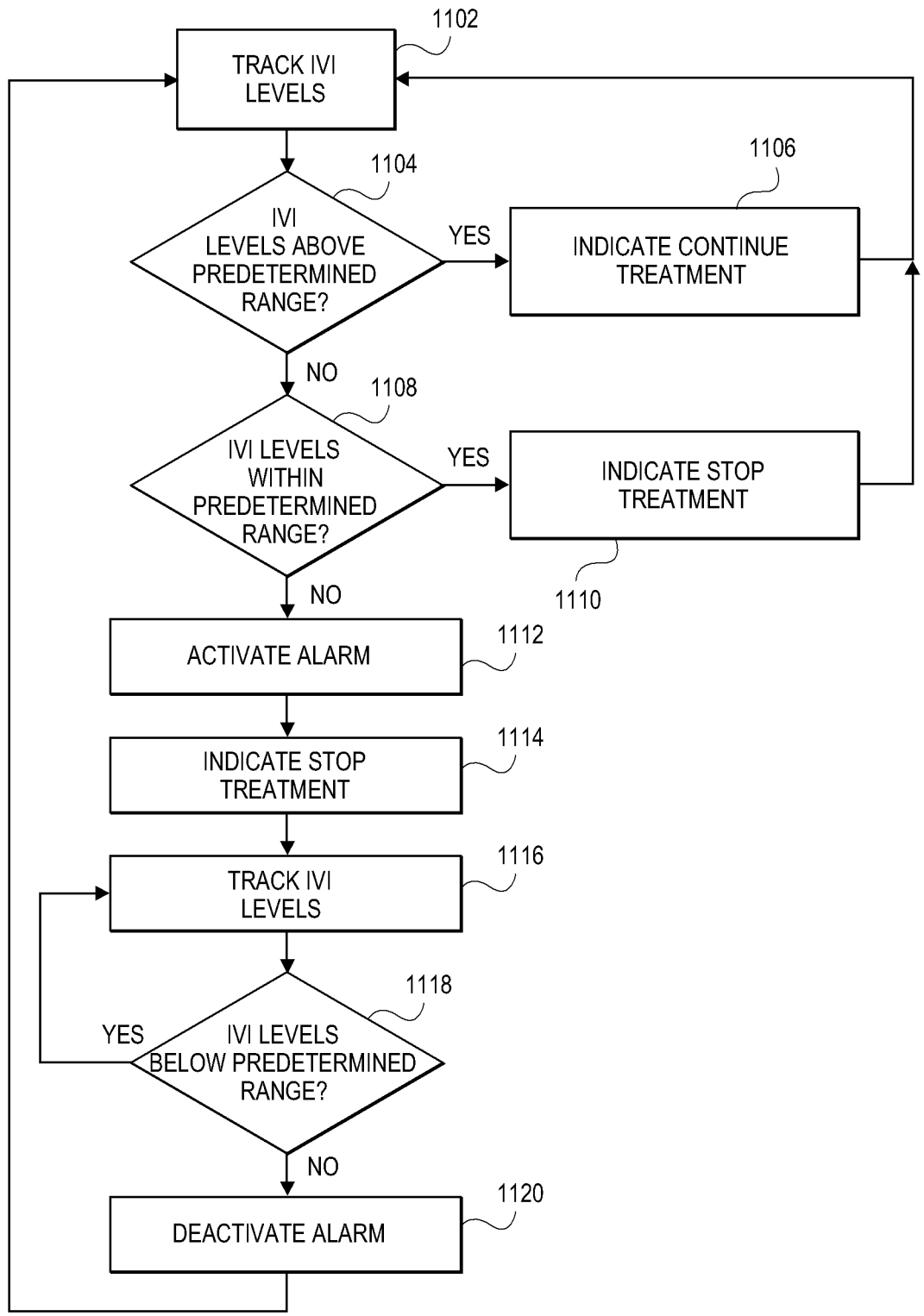
FIG. 11 is a flow diagram illustrative of another embodiment of a routine for indicating when a user should terminate treatment.

FIG. 11 is a flow diagram illustrative of another embodiment of a routine 1100 for indicating when a user should terminate treatment of a patient diagnosed with edema. Once a patient has been diagnosed with edema, a user can treat the patient in a number of ways including by, for example, administering a diuretic to remove the excess fluids. During the administration of the diuretic, the patient monitoring system 300 can track the IVI levels, as shown in block 1102. The patient monitoring system 300 can then determine if the IVI levels are above a predetermined range (also referred to as a first predetermined range) as shown in block 1104. If the IVI levels are above the predetermined range, the patient monitoring system 300 can indicate that the user can continue treatment, as shown in block 1106. As mentioned previously, treatment may include the administration of a diuretic among other things.

On the other hand, if the IVI levels are not above the predetermined range, the patient monitoring system 300 can determine if the IVI levels are within the predetermined range, as shown in block 1108. If the IVI levels are within the predetermined range, the patient monitoring system 300 can indicate to stop treatment, as illustrated in block 1110. In some embodiments, the patient monitoring system 300 indicates that no diuretic is needed. In certain embodiments, the patient monitoring system 300 can indicate that the user should cease administering the diuretic. In some embodiments, the patient monitoring system 300 can indicate that the user can continue administering the diuretic so long as the IVI levels remain within the predetermined range and/or within a second predetermined range, which can be smaller than and within the first predetermined range. The second predetermined range can be used to indicate when treatment should stop, while the patient is still exhibiting IVI levels within the first predetermined range. Further embodiments can include one or more features selected from any combination of the embodiments disclosed herein.

On the other hand, if the patient monitoring system 300 determines that the IVI levels are not within the predetermined range, the patient monitoring system 300 can activate an alarm indicating the IVI levels are below the predetermined range, as illustrated in block 1112. The alarm can be similar to the alarm described above with reference to FIG. 9. The patient monitoring system 300 can also indicate to stop treatment, as illustrated in block 1114 and described in greater detail above with reference to block 1110. As mentioned above, too much diuretic can cause dehydration, and IVI levels below the predetermined range can indicate dehydration.

At block 1116, the patient monitoring system 300 monitors and/or tracks the IVI levels. At decision block 1118, the patient monitoring system 300 can determine if the IVI levels remain below the predetermined range, and/or is within the second predetermined range. If the IVI levels remain below the predetermined range and/or outside the second predetermined range, the patient monitoring system 300 can continue tracking the IVI levels, as shown in block 1116. In addition, the patient monitoring system 300 can alter the alarm if the IVI levels remain below the predetermined range or outside the second predetermined range for a set amount of time or if the IVI levels get worse. On the other hand, if the patient monitoring system 300 determines that the IVI levels are no longer below the predetermined range and/or outside the second predetermined range, the patient monitoring system 300 can deactivate the alarm, as illustrated in block 1120, and continue tracking the IVI levels as illustrated in block 1102.

Additional, fewer, or different blocks, or any combination or variation thereof, can be used to implement the routine 1100 without departing from the spirit and scope of the description. For example, the routine 1100 can track impedance and/or weight levels of the patient and use those levels to help determine whether to indicate treatment should be continued or stopped. In an embodiment, the routine 1100 measures and tracks all three parameters of impedance, weight and IVI in order to determine the patient's condition. This providing a more robust indication of the patient's condition. Ranges for impedance and weight levels can be generated and used in a manner similar to the ranges for the IVI levels. Furthermore, it will be appreciated by those skilled in the art and others that the order of the blocks in FIG. 11 can be altered without departing from the spirit and scope of the description. Thus, the patient monitoring system 300 can determine simultaneously whether the IVI levels are above, below, and/or within the predetermined range. In some embodiments, the patient monitoring system 300 only determines whether the IVI levels are above, below, or within the predetermined range. In certain embodiments, one or more threshold values can be used as part of the predetermined ranges or as an alternative to the predetermined ranges. Further embodiments can include one or more features selected from any combination of the embodiments disclosed herein.

Figure 12:
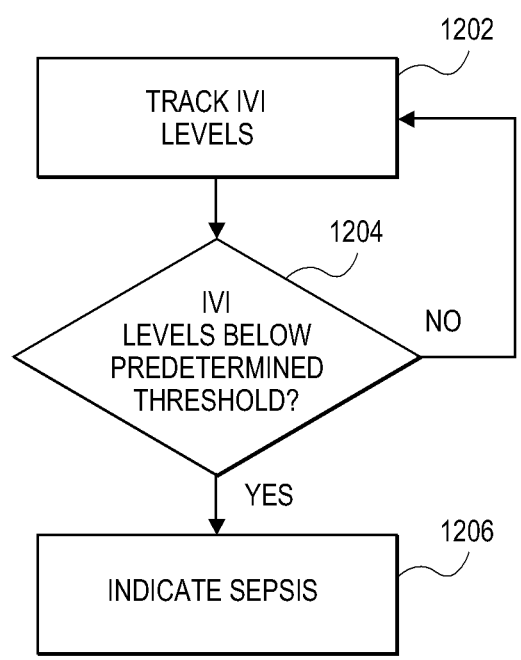
FIG. 12 is a flow diagram illustrative of an embodiment of a routine for indicating sepsis by tracking Pa levels.

FIG. 12 is a flow diagram illustrative of an embodiment of a routine 1200 for indicating sepsis based on IVI levels. Routine 1200 is similar in many respects to routine 900 except that IVI levels are being monitored for sepsis rather than edema, or heart failure. Block 1202 is similar to block 902 of FIG. 9. At decision block 1204, the patient monitoring system 300 determines if the IVI levels are below a predetermined threshold. As discussed previously, the predetermined threshold can be based on typical IVI levels of similarly situated patients, or can be different for each person and can be based on previously tracked data from that person, which takes into account the cyclical nature of that persons IVI levels. In some embodiments, the predetermined threshold is approximately 43 for males and approximately 52 for females. In certain embodiments, the threshold is based on a statistical analysis of the person's IVI levels. If the IVI levels have not fallen below the predetermined threshold, then the patient monitoring system 300 continues to track the IVI levels as, shown in block 1202.

On the other hand, if the IVI levels have fallen below the predetermined threshold the patient monitoring system 300 indicates the patient can be suffering from sepsis. As discussed above, the indication can occur in any number of ways including visual and audible cues as discussed in greater detail above with reference to FIG. 10. If the user is within visual or hearing range of the patient monitoring system 300, the patient monitoring system 300 can use a visual or auditory cue to alert the user. Alternatively, if the patient monitoring system 300 is remotely located from the user, the patient monitoring system 300 can communicate the indication or alarm using any number of communicative technologies, including, but not limited to an email, fax, voicemail, SMS message, page, instant message, or the like. For example, if the patient monitoring system 300 is located within the home of the patient and the IVI levels move below the predetermined threshold, the patient monitoring system 300 can send an email to the user of the patient indicating the previous and current IVI levels. Although not illustrated in FIG. 12, routine 1200 can also activate and deactivate an alarm as appropriate, as described above, with reference to FIG. 9.

Additional, fewer, or different blocks, or any combination or variation thereof, can be used to implement the routine 1200 without departing from the spirit and scope of the description. For example, the patient monitoring system 300 can indicate that fluids, such as IV fluids, should be administered to the patient. In some embodiments, the patient monitor can track the impedance of the patient or EVI levels. The impedance can indicate any changes in EVI and further improve the ability of the patient monitoring system 300 to detect sepsis. Other methods to track changes in EVI other than measuring impedance can also be used. Thus, by also tracking the EVI of a patient, the patient monitoring system 300 can be able to more accurately indicate sepsis. In some embodiments, pleth variability index is used to determine if a patient is suffering from sepsis. Further embodiments can include one or more features selected from any combination of the embodiments disclosed herein.

Figure 13:
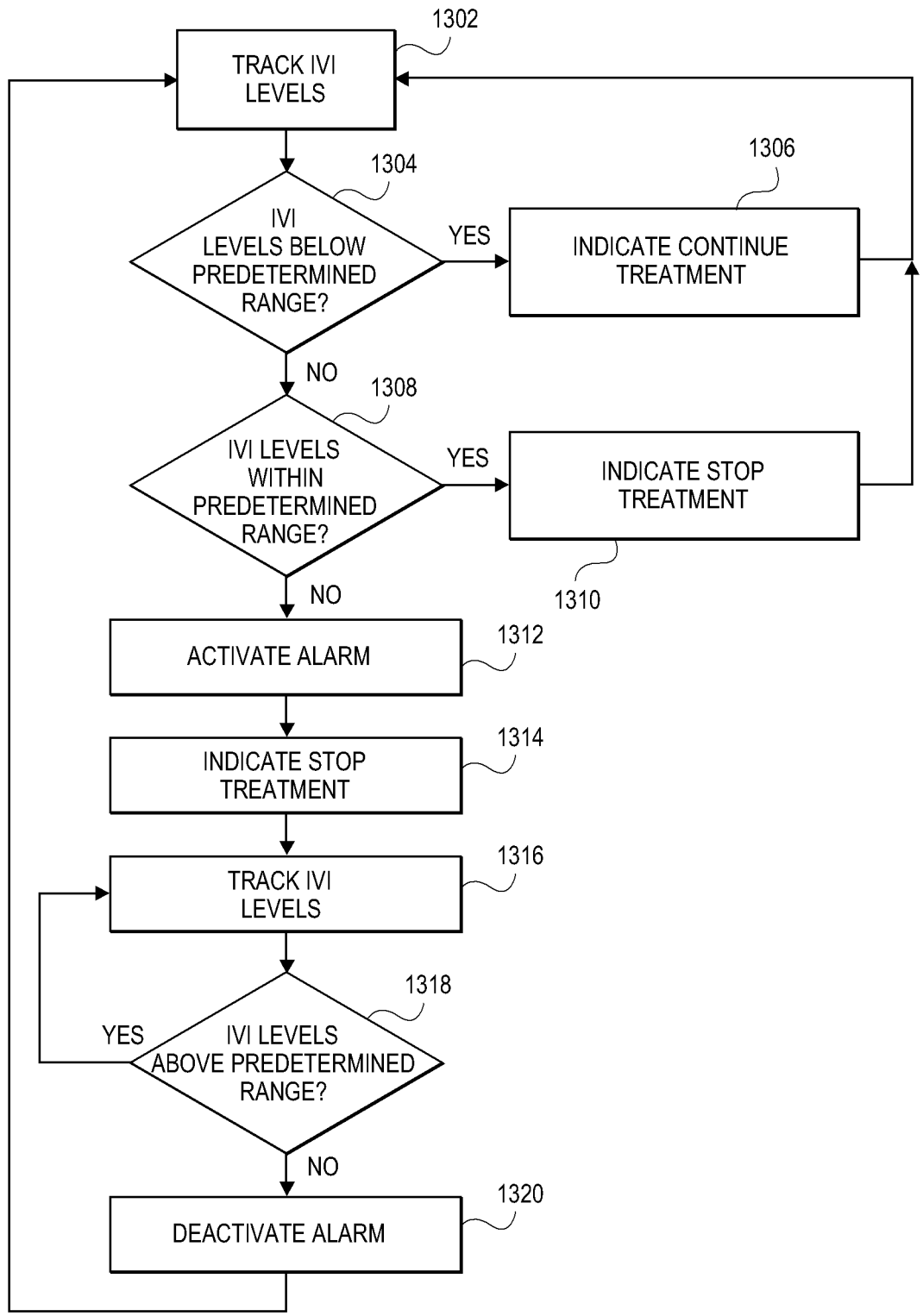
FIG. 13 is a flow diagram illustrative of another embodiment of a routine for indicating when a user should terminate treatment by tracking Pa levels.

FIG. 13 is a flow diagram illustrative of an embodiment of a routine 1300 for indicating when a user should terminate administering IV fluids to a patient during treatment of sepsis by tracking IVI levels. Once a patient has been diagnosed with sepsis, a user can begin treatment, such as by administering IV fluids to increase blood pressure. During the treatment, the patient monitoring system 300 can track the IVI levels, as shown in block 1302. The patient monitoring system 300 can then determine if the IVI levels are below a predetermined range (also referred to as a first predetermined range) as shown in block 1304. If the IVI levels are below the predetermined range, the patient monitoring system 300 can indicate that the user can continue treatment, as shown in block 1306. As mentioned previously, treatment may include the administration of fluids, such as IV fluids, among other things.

On the other hand, if the IVI levels are not below the predetermined range the patient monitoring system 300 can determine if the IVI levels are within the predetermined range, as shown in block 1308. If the IVI levels are within the predetermined range, the patient monitoring system 300 can indicate to stop treatment, as illustrated in block 1310. In some embodiments, the patient monitoring system 300 indicates that no IV fluids are needed and/or that the user should cease administering the IV fluids. In some embodiments, the patient monitoring system 300 can indicate that the user can continue administering the IV fluids so long as the IVI levels remain within the predetermined range and/or within a second predetermined range, which can be smaller than and within the first predetermined range. The second predetermined range can be used to indicate when treatment should stop, while the patient is still exhibiting IVI levels within the first predetermined range. Further embodiments can include one or more features selected from any combination of the embodiments disclosed herein.

On the other hand, if the patient monitoring system 300 determines that the IVI levels are not within the predetermined range and/or the second predetermined range, the patient monitoring system 300 can activate an alarm indicating the IVI levels are above the predetermined range, as illustrated in block 1312. The alarm can be similar to the alarm described above with reference to FIG. 9. The patient monitoring system 300 can also indicate to stop treatment, as illustrated in block 1314 and described in greater detail above with reference to block 1310.

At block 1316, the patient monitoring system 300 can continue monitoring and/or tracking the IVI levels. At decision block 1318, the patient monitoring system 300 can determine if the IVI levels remain above the predetermined range and/or outside the second predetermined range. If the IVI levels remain above the predetermined range and/or outside the second predetermined range, the patient monitoring system 300 can continue tracking the IVI levels, as shown in block 1316. In addition, the patient monitoring system 300 can alter the alarm if the IVI levels remain above the predetermined range and/or outside the second predetermined range for a set amount of time or if the IVI levels worsen. On the other hand, if the patient monitoring system 300 determines that the IVI levels are no longer above the predetermined range and/or outside the second predetermined range, the patient monitoring system 300 can deactivate the alarm, as illustrated in block 1320, and continue tracking the IVI levels as illustrated in block 1302.

It will be appreciated by those skilled in the art and others that the order of the blocks in FIG. 13 can be altered without departing from the spirit and scope of the description. In some embodiments, the patient monitoring system 300 can determine simultaneously whether the IVI levels are above, below, and/or within the predetermined range. In certain embodiments, the patient monitoring system 300 only determines whether the IVI levels are above, below, or within the predetermined range.

Furthermore, additional, fewer, or different blocks, or any combination or variation thereof, can be used to implement the routine 1300 without departing from the spirit and scope of the description. For example, routine 1200 can be combined with routine 1300. In some embodiments, alarms can be activated while fluids are being administered and deactivated when the IVI levels are within the predetermined range. In some embodiments, routine 1300 only monitors IVI levels to determine if the IVI levels are below the predetermined threshold and sounds an alarm when the IVI levels are below the predetermined threshold, i.e. the routine 1300 may not monitor or sound an alarm if the IVI levels drop above the predetermined threshold. In certain embodiments, the routine 1300 can include tracking impedance and/or weight levels of the patient. The routine 1300 can include the impedance and/or weight levels of the patient in determining when to activate and deactivate the alarm. For example, a decrease in impedance can indicate and increased likelihood of sepsis when IVI levels are below the predetermined range. In some embodiments, one or more threshold values can be used as part of the predetermined ranges or as an alternative to the predetermined ranges. The patient monitoring system 300 can activate the alarm in light of the decrease in impedance. Further embodiments can include one or more features selected from any combination of the embodiments disclosed herein.

Figure 14:
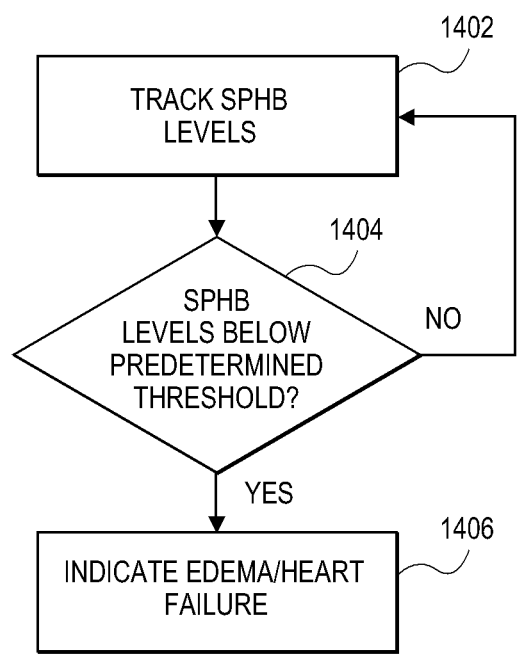
FIG. 14 is a flow diagram illustrative of an embodiment of a routine for indicating edema or heart failure.

FIG. 14 is a flow diagram illustrative of an embodiment of a routine 1400 for indicating edema or heart failure based on SpHb levels. At block 1402 the patient monitoring system 300 tracks SpHb levels. At decision block 1404, the patient monitoring system 300 determines if the SpHb levels are below a predetermined threshold. As discussed previously, the predetermined threshold can be based on typical SpHb levels of similarly situated patients, or can be different for each person and can be based on previously tracked data from that person, which takes into account the cyclical nature of that persons SpHb levels. If the SpHb levels are not below the predetermined threshold, then the patient monitoring system 300 continues to track the SpHb levels as, shown in block 1402.

On the other hand, if the SpHb levels are below the predetermined threshold the patient monitoring system 300 indicates the patient can be suffering from edema and/or heart failure. The user may be the patient, a healthcare provider, a service center, or the like. As discussed above, the indication can occur in any number of ways including visual and audible cues. If the user is within visual or hearing range of the patient monitoring system 300, the patient monitoring system 300 can use a visual or auditory cue to alert the user. Alternatively, if the patient monitoring system 300 is remotely located from the user, the patient monitoring system 300 can communicate the indication or alarm using any number of communicative technologies, including, but not limited to an email, fax, voicemail, SMS message, page, instant message, or the like. For example, if the patient monitoring system 300 is located within the home of the patient and the SpHb levels are below the predetermined threshold, the patient monitoring system 300 can send an email to the user of the patient indicating the previous and current SpHb levels. Although not illustrated in FIG. 14, routine 1400 can also activate and deactivate an alarm as appropriate, as described above, with reference to FIG. 9.

Furthermore, additional, fewer, or different blocks, or any combination or variation thereof, can be used to implement the routine 1400 without departing from the spirit and scope of the description. For example, the patient monitoring system 300 can indicate that a diuretic should be administered to the patient. In some embodiments, the patient monitoring system 300 tracks the weight, impedance, and/or EVI of the patient in addition to SpHb. An increase in weight is another indication of edema as is an increase in impedance. In addition, the impedance can indicate any changes in EVI and be used to detect sepsis. Other methods to track changes in EVI other than measuring impedance can also be used. By tracking the weight, impedance, and/or EVI of a patient, the patient monitor can be able to more accurately indicate edema and/or heart failure. Thresholds for the impedance and weight can be generated and used similar to the SpHb thresholds. The patient monitoring system 300 can make a determination based on the various thresholds. Further embodiments can include one or more features selected from any combination of the embodiments disclosed herein.

Figure 15:
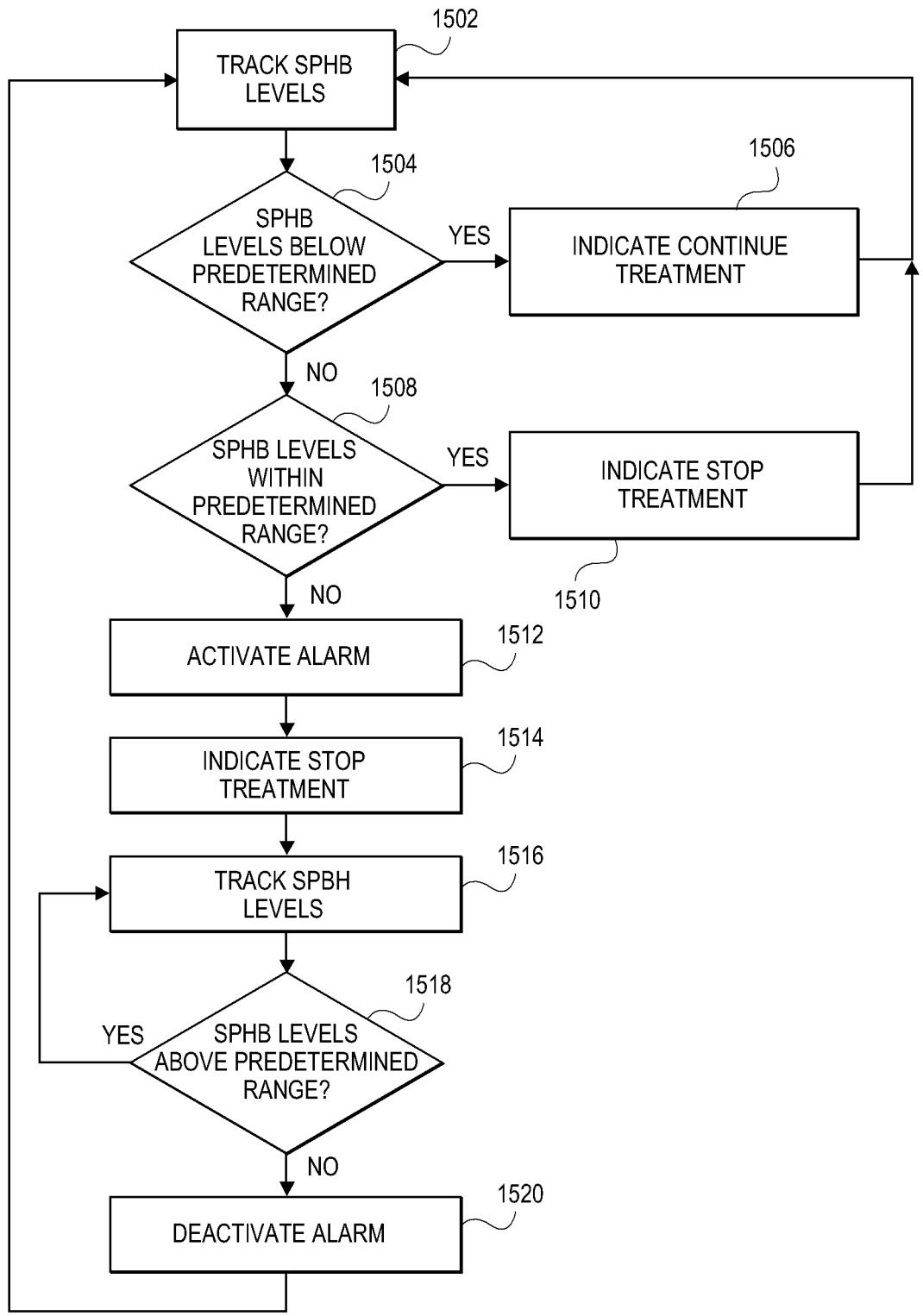
FIG. 15 is a flow diagram illustrative of another embodiment of a routine for indicating when a user should terminate treatment to a patient.

FIG. 15 is a flow diagram illustrative of another embodiment of a routine 1500 for indicating when a user should terminate treatment of a patient diagnosed with edema. Once a patient has been diagnosed with edema, a user can treat the patient in a number of ways including by, for example, administering a diuretic to remove the excess fluids. During the administration of the diuretic, the patient monitoring system 300 can track the SpHb levels, as shown in block 1502. The patient monitoring system 300 can then determine if the SpHb levels are below a predetermined range (also referred to as a first predetermined range) as shown in block 1504. If the SpHb levels are below the predetermined range, the patient monitoring system 300 can indicate that the user can continue treatment, as shown in block 1506. As mentioned previously, treatment may include the administration of a diuretic among other things.

On the other hand, if the Spat) levels are not below the predetermined range, the patient monitoring system 300 can determine if the SpHb levels are within the predetermined range, as shown in block 1508. If the SpHb levels are within the predetermined range, the patient monitoring system 300 can indicate to stop treatment, as illustrated in block 1510. In some embodiments, the patient monitoring system 300 indicates that no diuretic is needed. In certain embodiments, the patient monitoring system 300 can indicate that the user should cease administering the diuretic. In some embodiments, the patient monitoring system 300 can indicate that the user can continue administering the diuretic so long as the SpHb levels remain within the predetermined range and/or within a second predetermined range, which can be smaller than the first predetermined range. The second predetermined range can be used to indicate when treatment should stop, while the patient is still exhibiting SpHb levels within the first predetermined range. Further embodiments can include one or more features selected from any combination of the embodiments disclosed herein.

On the other hand, if the patient monitoring system 300 determines that the SpHb levels are not within the predetermined range, the patient monitoring system 300 can activate an alarm indicating the SpHb levels are above the predetermined range, as illustrated in block 1512. The alarm can be similar to the alarm described above with reference to FIG. 9. The patient monitoring system 300 can also indicate to stop treatment, as illustrated in block 1514 and described in greater detail above with reference to block 1510. As mentioned above, too much diuretic can cause dehydration, and SpHb levels above the predetermined range can indicate dehydration.

At block 1516, the patient monitoring system 300 monitors and/or tracks the SpHb levels. At decision block 1518, the patient monitoring system 300 can determine if the SpHb levels remain above the predetermined range, and/or is within the second predetermined range. If the SpHb levels remain above the predetermined range and/or outside the second predetermined range, the patient monitoring system 300 can continue tracking the SpHb levels, as shown in block 1516. In addition, the patient monitoring system 300 can alter the alarm if the SpHb levels remain above the predetermined range or outside the second predetermined range for a set amount of time or if the SpHb levels get worse. On the other hand, if the patient monitoring system 300 determines that the SpHb levels are no longer above the predetermined range and/or outside the second predetermined range, the patient monitoring system 300 can deactivate the alarm, as illustrated in block 1520, and continue tracking the SpHb levels as illustrated in block 1502.

Additional, fewer, or different blocks, or any combination or variation thereof, can be used to implement the routine 1500 without departing from the spirit and scope of the description. For example, the routine 1500 can track impedance and/or weight levels of the patient and use those levels to help determine whether to indicate treatment should be continued or stopped. Ranges for impedance and weight levels can be generated and used in a manner similar to the ranges for the SpHb levels. Furthermore, it will be appreciated by those skilled in the art and others that the order of the blocks in FIG. 15 can be altered without departing from the spirit and scope of the description. Thus, the patient monitoring system 300 can determine simultaneously whether the SpHb levels are above, below, and/or within the predetermined range. In some embodiments, the patient monitoring system 300 only determines whether the SpHb levels are above, below, or within the predetermined range. Further embodiments can include one or more features selected from any combination of the embodiments disclosed herein.

Figure 16:
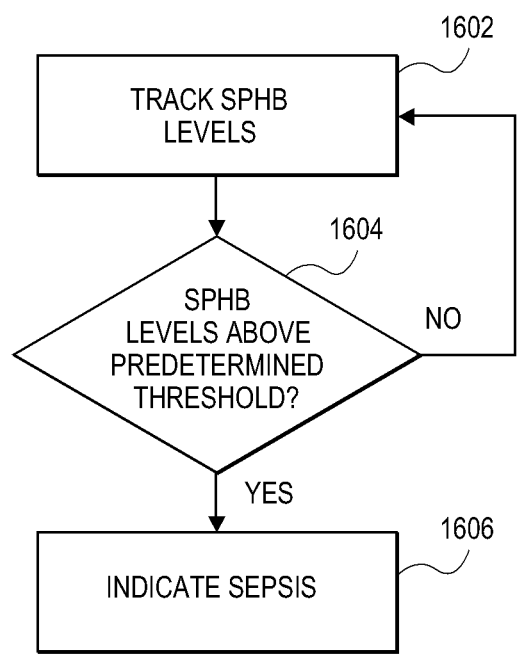
FIG. 16 is a flow diagram illustrative of an embodiment of a routine for indicating sepsis by tracking SpHb levels.

FIG. 16 is a flow diagram illustrative of an embodiment of a routine 1600 for indicating sepsis. Routine 1600 is similar in many respects to routine 900 except that SpHb levels are being monitored for sepsis rather than edema, or heart failure. Block 1602 is similar to block 902 of FIG. 9. At decision block 1604, the patient monitoring system 300 determines if the SpHb levels have are above a predetermined threshold. As discussed previously, the predetermined threshold can be based on typical SpHb levels of similarly situated patients, or can be different for each person and can be based on previously tracked data from that person, which takes into account the cyclical nature of that persons SpHb levels. If the SpHb levels have not are above the predetermined threshold, then the patient monitoring system 300 continues to track the SpHb levels as, shown in block 1602.

On the other hand, if the SpHb levels have are above the predetermined threshold the patient monitoring system 300 indicates the patient can be suffering from sepsis. As discussed above, the indication can occur in any number of ways including visual and audible cues as discussed in greater detail above with reference to FIG. 14, if the user is within visual or hearing range of the patient monitoring system 300, the patient monitoring system 300 can use a visual or auditory cue to alert the user. Alternatively, if the patient monitoring system 300 is remotely located from the user, the patient monitoring system 300 can communicate the indication or alarm using any number of communicative technologies, including, but not limited to an email, fax, voicemail, SMS message, page, instant message, or the like. For example, if the patient monitoring system 300 is located within the home of the patient and the SpHb levels move above the predetermined threshold, the patient monitoring system 300 can send an email to the user of the patient indicating the previous and current SpHb levels. Although not illustrated in FIG. 16, routine 1600 can also activate and deactivate an alarm as appropriate, as described above, with reference to FIG. 9.

Additional, fewer, or different blocks, or any combination or variation thereof, can be used to implement the routine 1600 without departing from the spirit and scope of the description. For example, the patient monitoring system 300 can indicate that fluids should be administered to the patient. In some embodiments, the patient monitor can track the impedance of the patient or EVI levels. The impedance can indicate any changes in EVI and further improve the ability of the patient monitoring system 300 to detect sepsis. Other methods to track changes in EVI other than measuring impedance can also be used. Thus, by also tracking the EVI of a patient, the patient monitoring system 300 can be able to more accurately indicate sepsis. In some embodiments, pleth variability index is used to determine if a patient is suffering from sepsis. Further embodiments can include one or more features selected from any combination of the embodiments disclosed herein.

Figure 17:
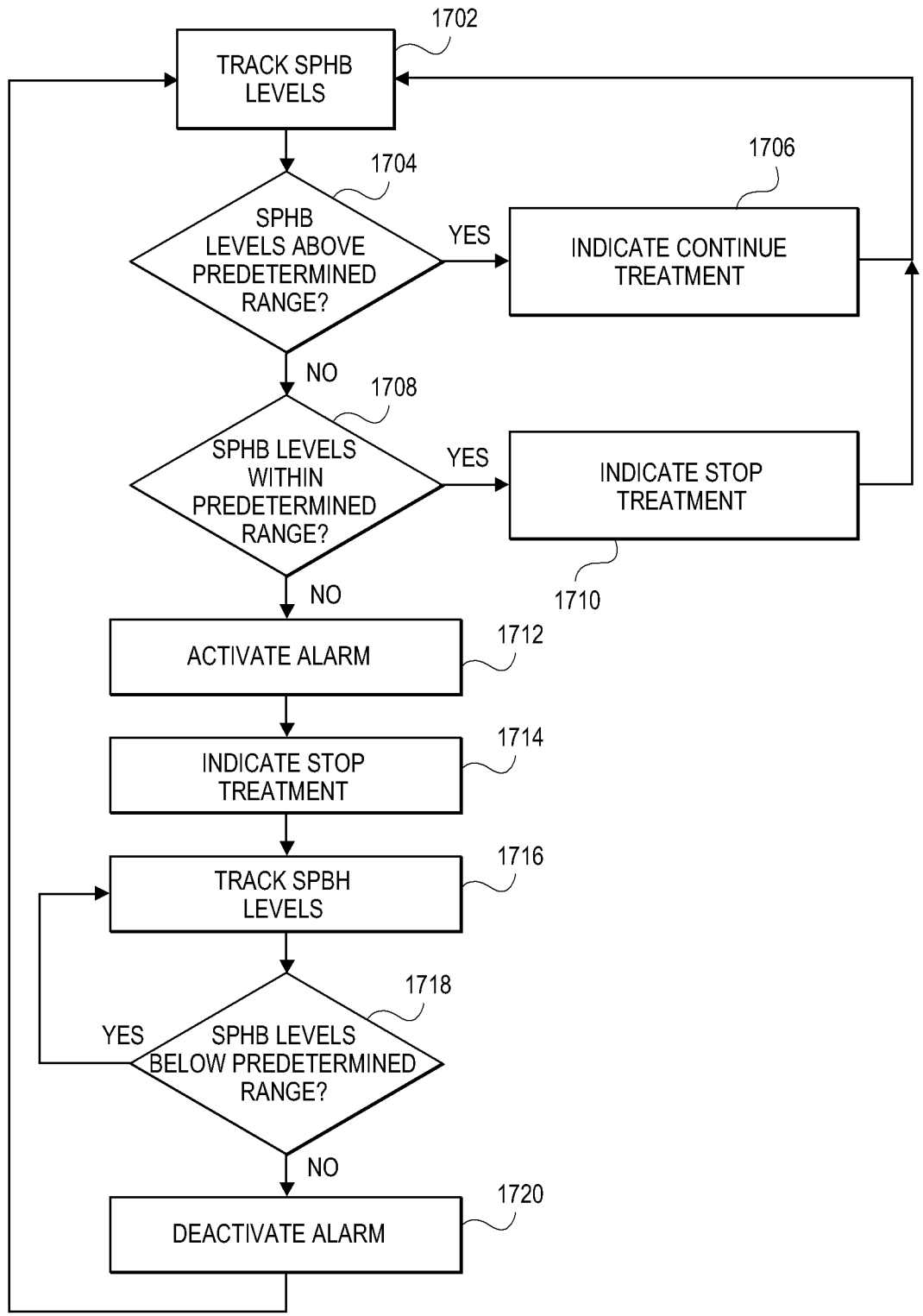
FIG. 17 is a flow diagram illustrative of another embodiment of a routine for indicating when a user should terminate treatment by tracking SpHb levels.

FIG. 17 is a flow diagram illustrative of an embodiment of a routine 1700 for indicating when a user should terminate administering IV fluids to a patient during treatment of sepsis by tracking SpHb levels. Once a patient has been diagnosed with sepsis, a user can begin treatment, such as by administering IV fluids to increase blood pressure. During the treatment, the patient monitoring system 300 can track the SpHb levels, as shown in block 1702. The patient monitoring system 300 can then determine if the SpHb levels are above a predetermined range (also referred to as a first predetermined range) as shown in block 1704. If the SpHb levels are above the predetermined range, the patient monitoring system 300 can indicate that the user can continue treatment, as shown in block 1706. As mentioned previously, treatment may include the administration of fluids, such as IV fluids, among other things.

On the other hand, if the SpHb levels are not above the predetermined range the patient monitoring system 300 can determine if the Spat) levels are within the predetermined range, as shown in block 1708. If the SpHb levels are within the predetermined range, the patient monitoring system 300 can indicate to stop treatment, as illustrated in block 1710. In some embodiments, the patient monitoring system 300 indicates that no IV fluids are needed and/or that the user should cease administering the IV fluids. In some embodiments, the patient monitoring system 300 can indicate that the user can continue administering the IV fluids so long as the SpHb levels remain within the predetermined range and/or within a second predetermined range, which can be smaller than the first predetermined range. The second predetermined range can be used to indicate when treatment should stop, while the patient is still exhibiting SpHb levels within the first predetermined range. Further embodiments can include one or more features selected from any combination of the embodiments disclosed herein.

On the other hand, if the patient monitoring system 300 determines that the SpHb levels are not within the predetermined range and/or the second predetermined range, the patient monitoring system 300 can activate an alarm indicating the SpHb levels are below the predetermined range, as illustrated in block 1712. The alarm can be similar to the alarm described above with reference to FIG. 9. The patient monitoring system 300 can also indicate to stop treatment, as illustrated in block 1714 and described in greater detail above with reference to block 1710.

At block 1716, the patient monitoring system 300 can continue monitoring and/or tracking the SpHb levels. At decision block 1718, the patient monitoring system 300 can determine if the SpHb levels remain below the predetermined range and/or outside the second predetermined range. If the SpHb levels remain below the predetermined range and/or outside the second predetermined range, the patient monitoring system 300 can continue tracking the SpHb levels, as shown in block 1716. In addition, the patient monitoring system 300 can alter the alarm if the SpHb levels remain below the predetermined range and/or outside the second predetermined range for a set amount of time or if the SpHb levels worsen. On the other hand, if the patient monitoring system 300 determines that the SpHb levels are no longer below the predetermined range and/or outside the second predetermined range, the patient monitoring system 300 can deactivate the alarm, as illustrated in block 1720, and continue tracking the SpHb levels as illustrated in block 1702.

It will be appreciated by those skilled in the art and others that the order of the blocks in FIG. 17 can be altered without departing from the spirit and scope of the description. In some embodiments, the patient monitoring system 300 can determine simultaneously whether the SpHb levels are above, below, and/or within the predetermined range. In certain embodiments, the patient monitoring system 300 only determines whether the SpHb levels are above, below, or within the predetermined range.

Furthermore, additional, fewer, or different blocks, or any combination or variation thereof can be used to implement the routine 1700 without departing from the spirit and scope of the description. For example, routine 1600 can be combined with routine 1700. In some embodiments, alarms can be activated while fluids are being administered and deactivated when the SpHb levels are within the predetermined range. In some embodiments, routine 1700 only monitors SpHb levels to determine if the SpHb levels are above the predetermined threshold and sounds an alarm when the SpHb levels are above the predetermined threshold, i.e. the routine 1700 may not monitor or sound an alarm if the SpHb levels drop below the predetermined threshold. In certain embodiments, the routine 1700 can include tracking impedance levels of the patient. The routine 1700 can include the impedance levels of the patient in determining when to activate and deactivate the alarm. For example, a decrease in impedance can indicate and increased likelihood of sepsis when SpHb levels are above the predetermined range. The patient monitoring system 300 can activate the alarm in light of the decrease in impedance. Further embodiments can include one or more features selected from any combination of the embodiments disclosed herein.

Reference throughout this specification to "some embodiments," "certain embodiments," or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The various illustrative logical blocks, modules, data structures, and processes described herein may be implemented as electronic hardware, computer software, or combinations of both. To clearly illustrate this interchangeability of hardware and software, various illustrative components, blocks, modules, and states have been described above generally in terms of their functionality. However, while the various modules are illustrated separately, they may share some or all of the same underlying logic or code. Certain of the logical blocks, modules, and processes described herein may instead be implemented monolithically.

The various illustrative logical blocks, modules, data structures, and processes described herein may be implemented or performed by a machine, such as a computer, a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor may be a microprocessor, a controller, a microcontroller, a state machine, combinations of the same, or the like. A processor may also be implemented as a combination of computing devices for example, a combination of a DSP and a microprocessor, a plurality of microprocessors or processor cores, one or more graphics or stream processors, one or more microprocessors in conjunction with a DSP, or any other such configuration.

The blocks or states of the processes described herein may be embodied directly in hardware, in a software module executed by a processor, or in a combination of the two. For example, each of the processes described above may also be embodied in, and fully automated by, software modules executed by one or more machines such as computers or computer processors. A module may reside in a computer-readable storage medium such as RAM memory, flash memory, RUM memory, EPROM memory, EEPROM memory, registers, a hard disk, a removable disk, a. CD-ROM, memory capable of storing firmware, or any other form of computer-readable storage medium. An exemplary computer-readable storage medium can be coupled to a processor such that the processor can read information from, and write information to, the computer readable storage medium. In the alternative, the computer-readable storage medium may be integral to the processor. The processor and the computer-readable storage medium may reside in an ASIC.

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the logical blocks, modules, and processes illustrated may be made without departing from the spirit of the disclosure. As will be recognized, certain embodiments of the inventions described herein may be embodied within a form that does not provide all of the features and benefits set forth herein, as some features may be used or practiced separately from others.

What is claimed is:

1. A non-invasive multi-parameter patient monitoring system configured to determine a termination range for administering a diuretic, the non-invasive multi-parameter patient monitoring system comprising:
   a first and second emitter configured to emit light of at least two wavelengths through tissue of a patient;
   a detector configured to sense the light after it has passed through the tissue of the patient and to generate a signal indicative of the sensed light; and
   a patient monitor comprising:
      a sensor interface configured to receive the generated signal from the detector, and
      a processor configured to:
         determine, during administration of a diuretic to the patient, a measure of hemoglobin based at least in part on the generated signal, and
         determine an intravascular volume index (IVI) level based at least in part on the measure of hemoglobin,
         wherein the patient monitor is configured to provide an indication to terminate the administration of the diuretic based at least in part on a determination that the IVI level satisfies a threshold.

2. The system of claim 1, wherein the threshold is a predetermined threshold and wherein the predetermined threshold is approximately 61 for adult males and 64 for adult females.

3. The system of claim 1, wherein the threshold is a patient-specific IVI threshold.

4. The system of claim 1, wherein the IVI level is determined based at least in part on an amount of light detected by the detector.

5. The system of claim 1, further comprising a host instrument configured to activate an alert based at least in part on the determination that the IVI level of the plurality of IVI levels satisfies the threshold.

6. The system of claim 1, wherein the processor is further configured to determine a progress of edema based at least in part on the IVI level of the plurality of IVI levels.

7. The system of claim 1, wherein to determine the IVI level based at least in part on the measure of hemoglobin, the processor is configured to:
   determine a hematocrit value by multiplying the measure of hemoglobin by a first fixed value; and
   determine the IVI level by subtracting the hematocrit value from a second fixed value.

8. The system of claim 1, wherein the threshold is a first threshold, wherein the processor is configured to:
   determine at least one of a measure of impedance of the patient or a measure of weight of the patient,
   wherein the processor is configured to provide the indication to terminate the administration of the diuretic further based at least in part on a determination that the at least one of the measure of impedance of the patient or the measure of weight of the patient satisfies a second threshold.

9. The system of claim 1, wherein the measure of hemoglobin comprises total hemoglobin (SpHb).

10. The system of claim 1, wherein the IVI level is a current IVI level, wherein the processor is further configured to determine the patient-specific IVI threshold based at least in part on at least one previous IVI level of the patient, wherein the at least one previous IVI level of the patient is determined prior to the current IVI level.

11. A method for determining to terminate an administration of a diuretic using a non-invasive multi-parameter patient monitor, the method comprising:

determining, during administration of a diuretic to a patient, a plurality of measures of hemoglobin over a time period based at least in part on an intensity signal generated by a non-invasive sensing device attached to a tissue site of the patient;

determining a plurality of intravascular volume index (IVI) levels over the time period based at least in part on the plurality of measures of hemoglobin, wherein a particular IVI level corresponds to a particular measure of hemoglobin;

determining that an IVI level of the plurality of IVI levels satisfies a threshold; and providing an indication to terminate the administration of the diuretic based at least in part on the determination that the IVI level of the plurality of IVI levels satisfies the threshold.

12. The method of claim 11, wherein said providing the indication to terminate the administration of the diuretic comprises terminating administration of the diuretic.

13. The method of claim 11, further comprising determining the threshold based at least in part on at least some of the plurality of IVI levels.

14. The method of claim 13, wherein the threshold is a first threshold, the method further comprising:

determining a second threshold based at least in part on the plurality of IVI levels; and activating an alarm based at least in part on a determination that a current IVI level satisfies a second threshold.

15. The method of claim 11, wherein the threshold is a first threshold, further comprising:

determining at least one of a measure of impedance of the patient or a measure of weight of the patient, wherein said providing an indication to terminate the administration of the diuretic is further based at least in part on a determination that the at least one of the measure of impedance of the patient or the measure of weight of the patient satisfies a second threshold.

16. A non-invasive multi-parameter patient monitoring system configured to determine to terminate an administration of fluids to a patient, the non-invasive multi-parameter patient monitoring system comprising:

a sensor having at least one emitter and a detector configured to attach to a tissue site, the detector providing a detector signal responsive to an intensity of energy from the emitter after it has passed through the tissue site of a patient; and a patient monitor comprising:

a sensor interface configured to receive the detector signal from the sensor; and a processor configured to:

determine, during administration of fluids to the patient, a plurality of measures of hemoglobin over a time period based at least in part on the detector signal, determine a plurality of intravascular volume index (IVI) levels of a patient over the time period based at least in part on the plurality of measures of hemoglobin, and provide an indication to terminate the administration of the fluids based at least in part on a determination that an IVI level of the plurality of IVI levels satisfies a threshold.

17. The non-invasive multi-parameter patient monitoring system of claim 16, wherein the sensor is a first sensor, wherein the system further comprises an impedance sensor configured to transmit impedance signals of the patient to the processor, wherein the processor is further configured to determine one or more impedance levels of the patient and compute an extravascular volume index (EVI) level using the impedance levels, wherein to determine to provide the indication to terminate the administration of the fluids is further based at least in part on the EVI level.

18. The system of claim 16, wherein the one or more processors are further configured to terminate the administration of the fluids.

19. The system of claim 16, wherein the processor is further configured to determine a progress of sepsis based at least in part on the IVI level of the plurality of IVI levels.

* * * * *